United States Patent
Iida et al.

(10) Patent No.: US 7,274,016 B2
(45) Date of Patent: Sep. 25, 2007

(54) LIQUID SWITCH, AND MICROCHIP AND MASS-ANALYZING SYSTEM USING THE SAME

(75) Inventors: Kazuhiro Iida, Tokyo (JP); Masakazu Baba, Tokyo (JP); Hisao Kawaura, Tokyo (JP); Toru Sano, Tokyo (JP); Noriyuki Iguchi, Tokyo (JP); Hiroko Someya, Tokyo (JP); Wataru Hattori, Tokyo (JP); Minoru Asogawa, Tokyo (JP)

(73) Assignee: NEC Corporation, Tokyo (JP)

( * ) Notice: Subject to any disclaimer, the term of this patent is extended or adjusted under 35 U.S.C. 154(b) by 289 days.

(21) Appl. No.: 10/537,295

(22) PCT Filed: Dec. 2, 2003

(86) PCT No.: PCT/JP03/15416

§ 371 (c)(1),
(2), (4) Date: Jun. 2, 2005

(87) PCT Pub. No.: WO2004/051229

PCT Pub. Date: Jun. 17, 2004

(65) Prior Publication Data

US 2006/0102836 A1 May 18, 2006

(30) Foreign Application Priority Data

Dec. 2, 2002 (JP) .............................. 2002-350521

(51) Int. Cl.
*G01N 21/69* (2006.01)
*H01J 49/00* (2006.01)
*B01D 59/44* (2006.01)

(52) U.S. Cl. .................... 250/288; 250/428; 422/82; 210/635; 210/511; 137/268

(58) Field of Classification Search .................. None
See application file for complete search history.

(56) References Cited

U.S. PATENT DOCUMENTS

2006/0292039 A1* 12/2006 Iida .......................... 422/82.05

FOREIGN PATENT DOCUMENTS

JP 8-510597 11/1996

(Continued)

OTHER PUBLICATIONS

Sana, Baba, Iguchi, Iida, Kawaura, Sakamoto, Dai 63 Kai Extended Abstracts; The Japan Society of Applied Physics, separate vol. 3, Sep. 24, 2002, p. 1146 (25a-R-8).

(Continued)

*Primary Examiner*—Nikita Wells
(74) *Attorney, Agent, or Firm*—Young & Thompson

(57) ABSTRACT

A liquid sample (104) introduced in a main flow passage (101) is held in a dam portion (105), and a trigger liquid (106) is filled in a trigger flow passage (102). In this state, the trigger liquid (106) is further introduced at desired timing into the trigger flow passage (102) so that the front end portion of the level of the trigger liquid (106) is advanced and the front end portion is brought to be into contact with the dam portion (105). This causes the liquid sample (104) to move to the right (downstream side) in the figure, resulting in the liquid sample (104) flowing out to the downstream side of the main flow passage (101). This means that the trigger liquid (106) provides priming to realize a liquid switch.

28 Claims, 27 Drawing Sheets

FOREIGN PATENT DOCUMENTS

| | | |
|---|---|---|
| JP | 10-132712 | 5/1998 |
| JP | 2001-503854 | 3/2001 |
| JP | 2001-264297 | 9/2001 |
| JP | 2001-515216 | 9/2001 |
| JP | 2001-518614 | 10/2001 |
| JP | 2002-207031 | 7/2002 |
| JP | 2002-236108 | 8/2002 |
| JP | 2002-524755 | 8/2002 |
| JP | 2002-257838 | 9/2002 |
| WO | WO 01/02737 | 1/2001 |

OTHER PUBLICATIONS

M. Baba, T. Sano, N. Iguchi, K. Iida, T. Sakamoto, H. Kawaura, Sixth International Conference on Miniaturized Chemical and Biochemical Analysis Systems (Micro Total Analysis Systems 2002), Nov. 3, 2002, vol. 2, pp. 763 to 765.

* cited by examiner 121  122  105

FIG. 4
(a)
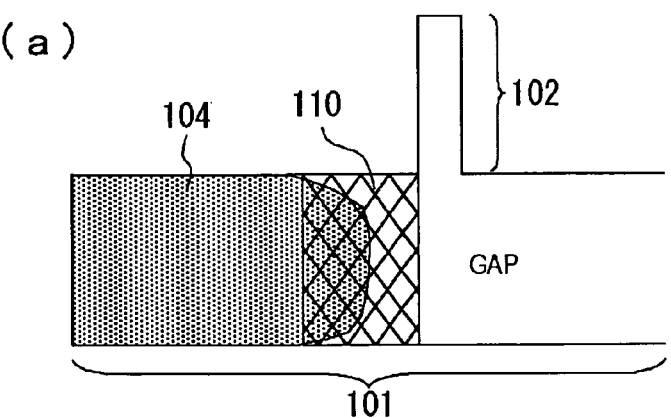
(b)
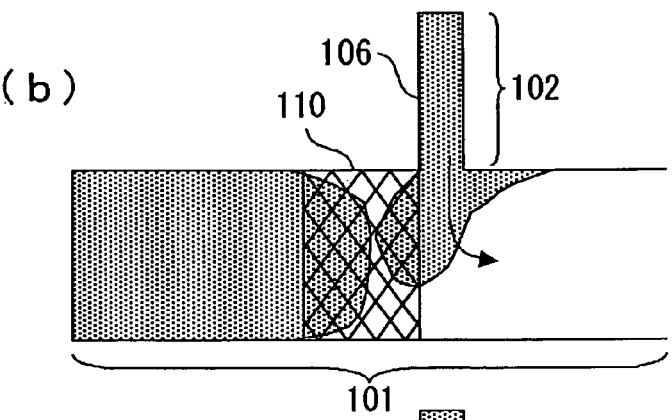
(c)
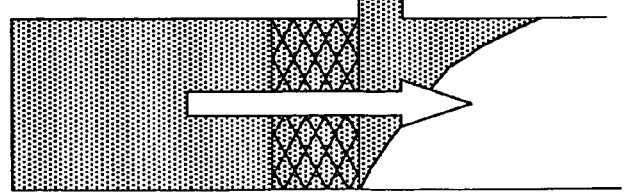

192  191

101

600

FIG. 11
(a)
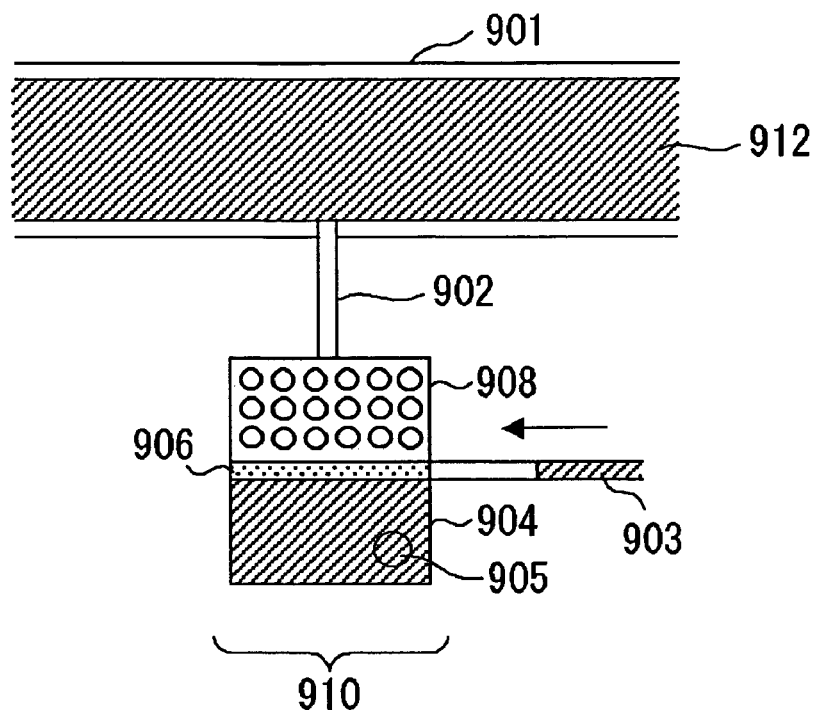
(b)
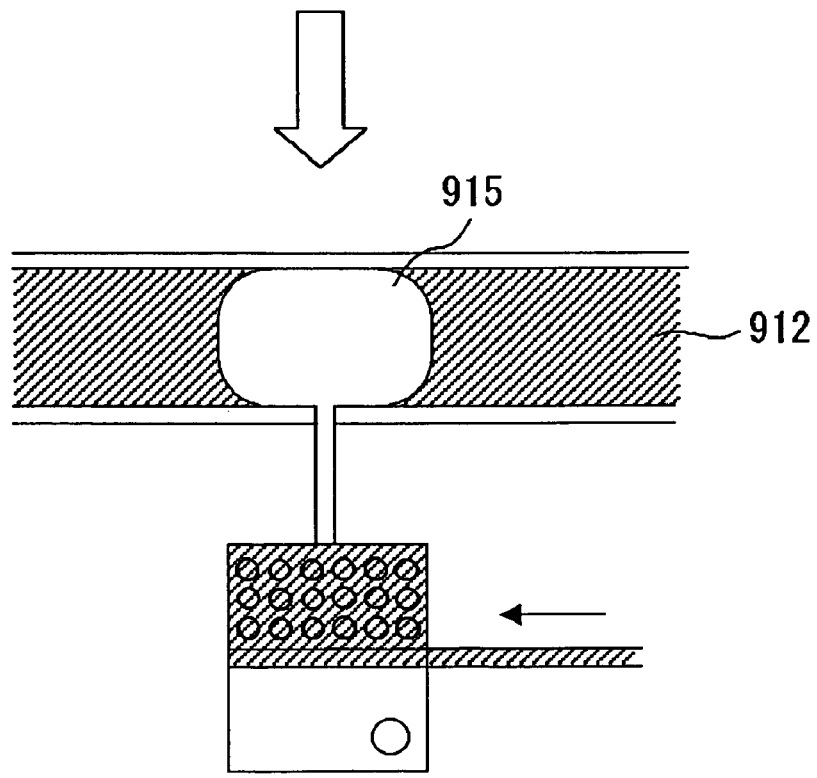

FIG. 12
(a)
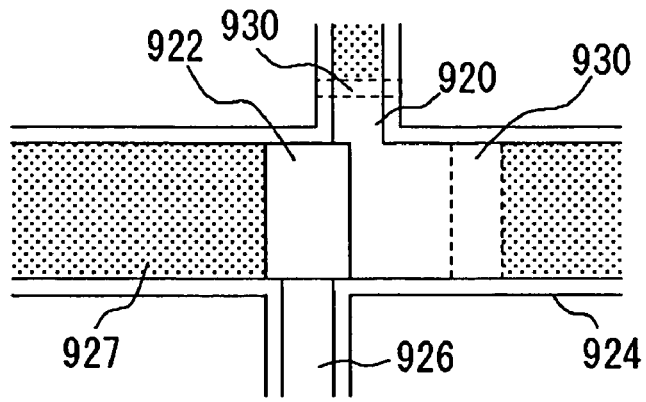
(b)
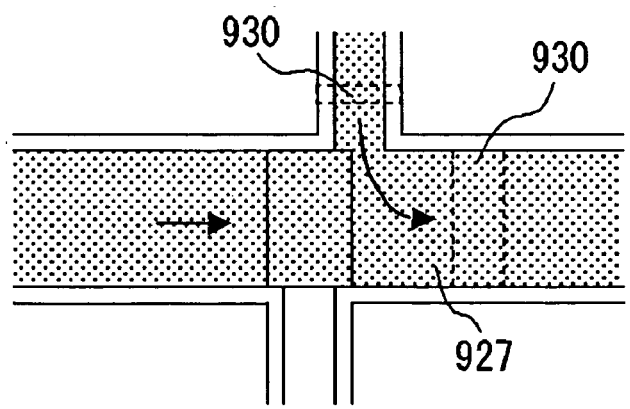
(c)
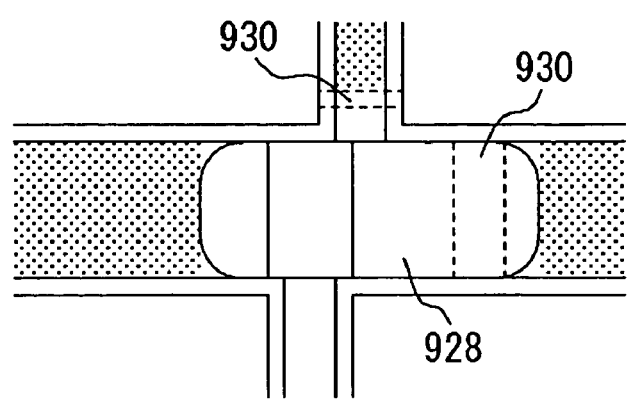

FIG. 14
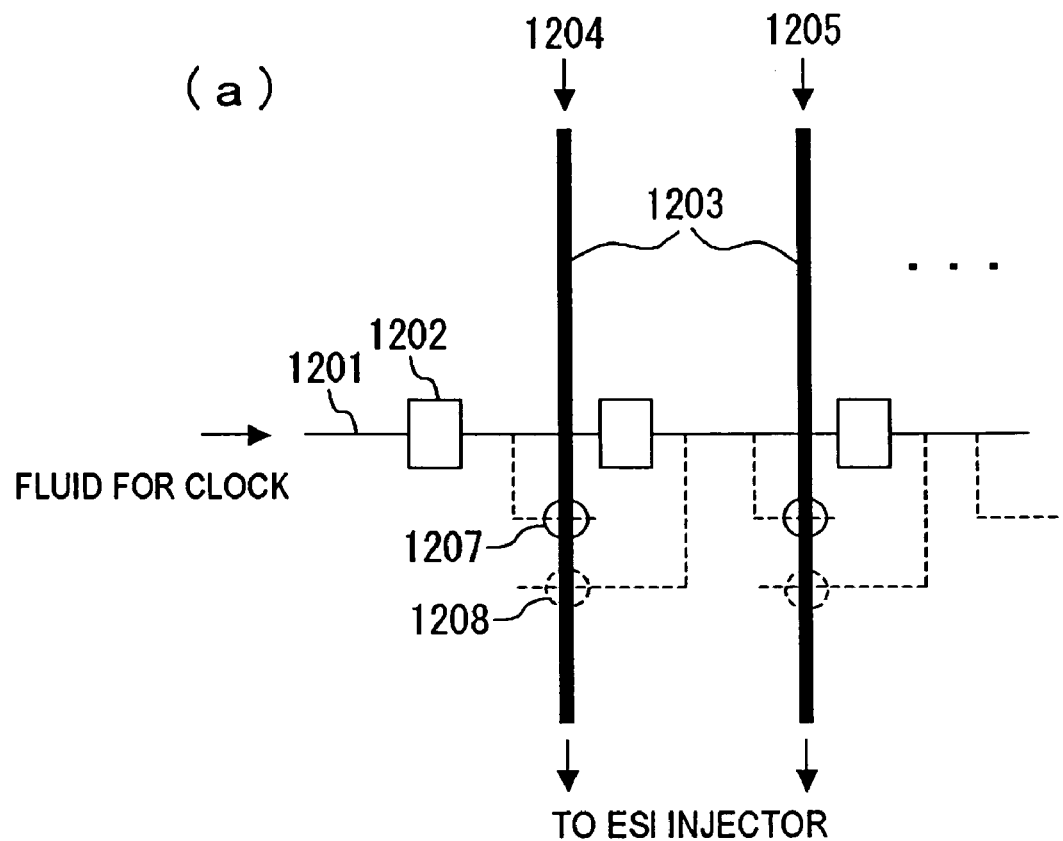
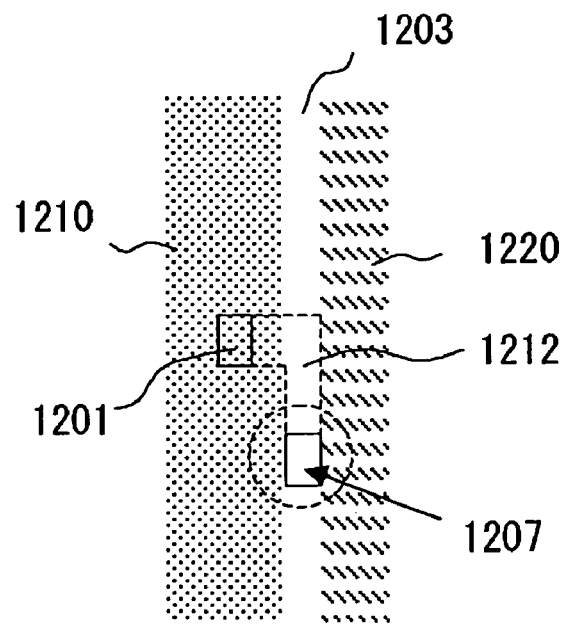

FIG. 15
(a)
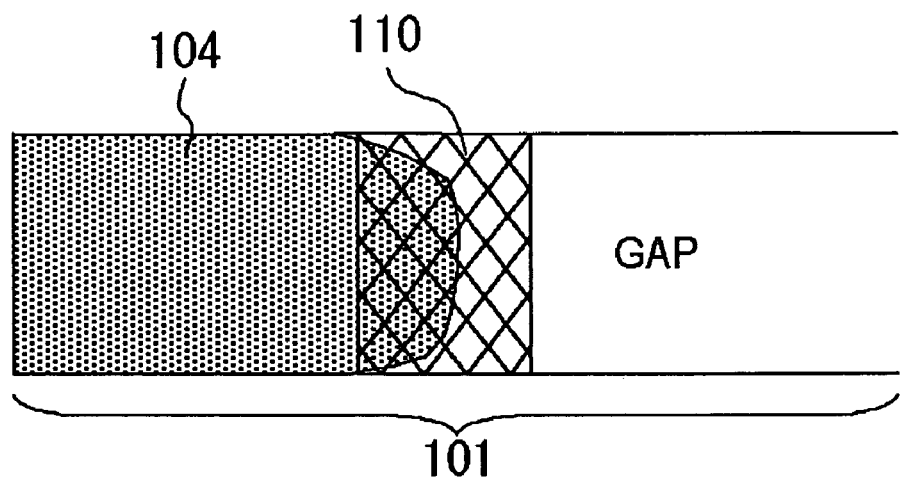
(b)
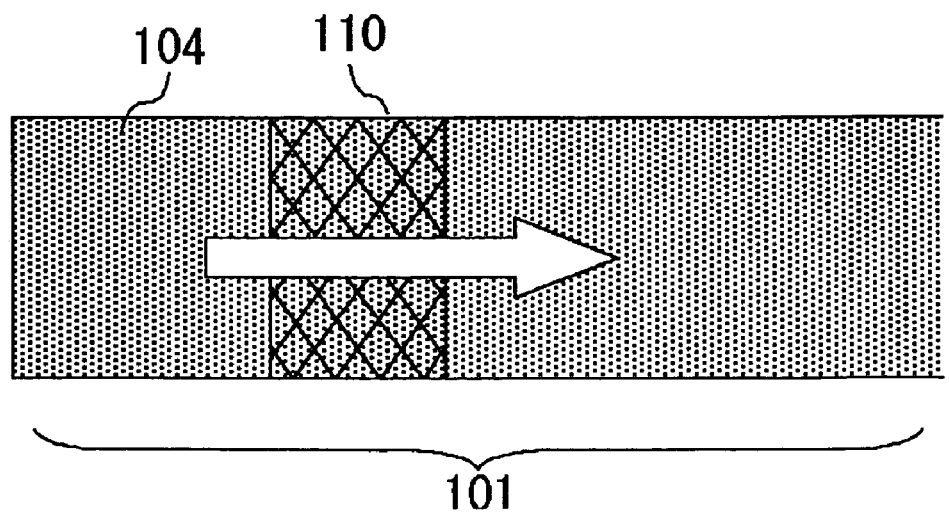

FIG. 18
(a)
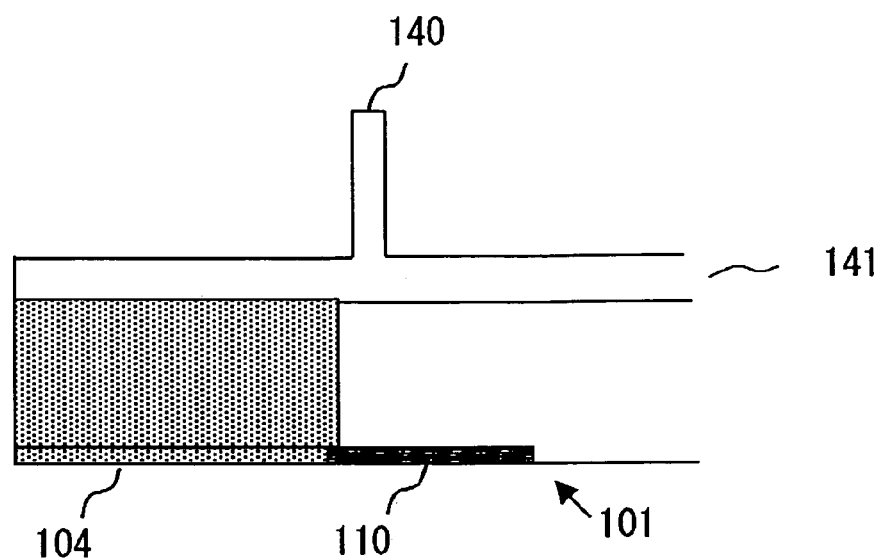
(b)
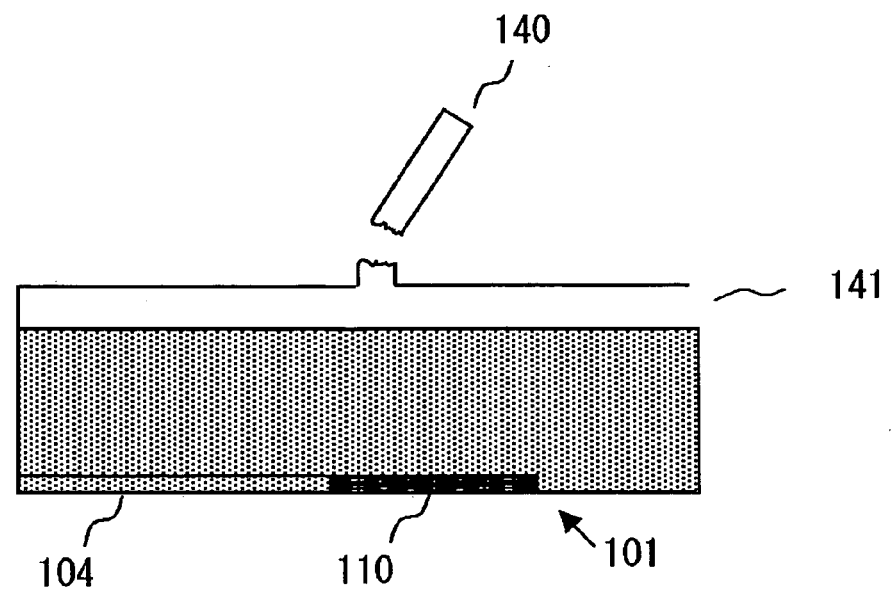

FIG. 21
(A)
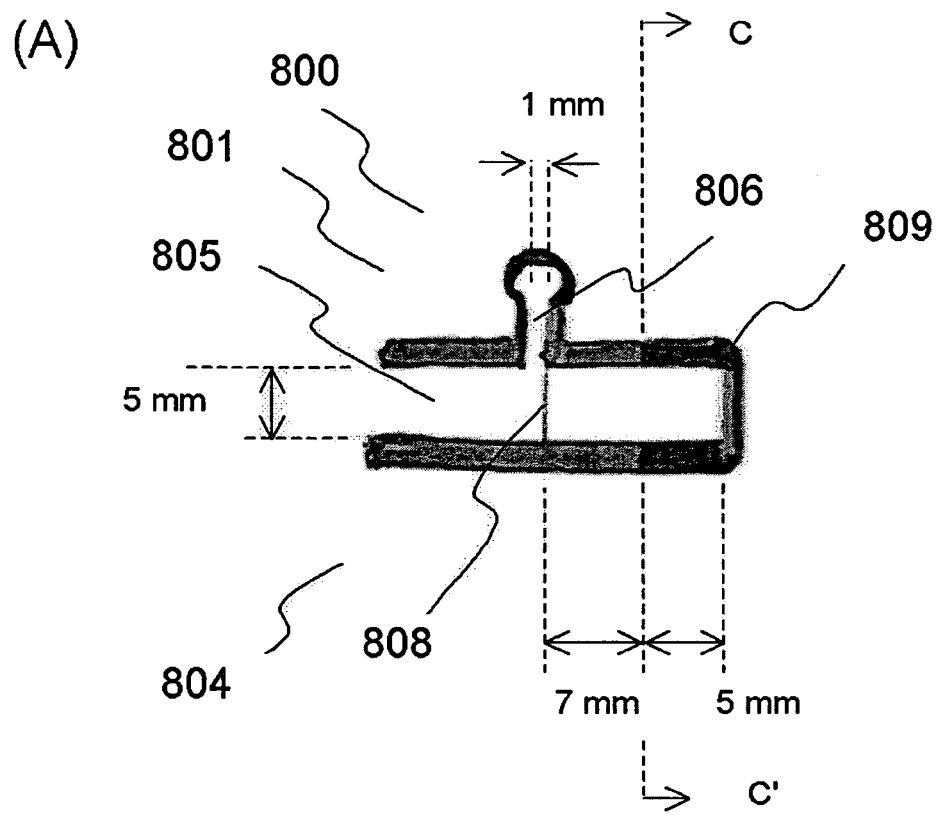
(B) C-C' CROSS-SECTIONAL VIEW
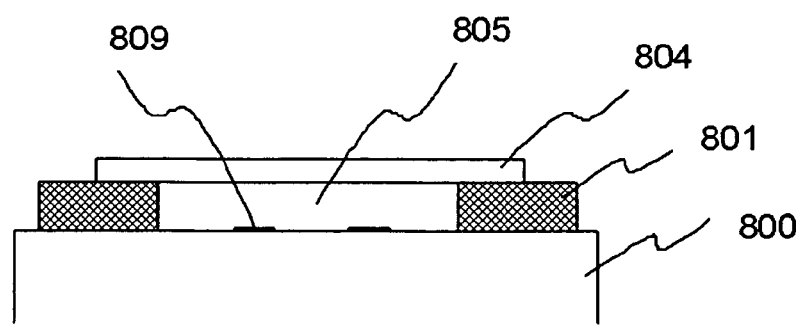

FIG. 22
(A)
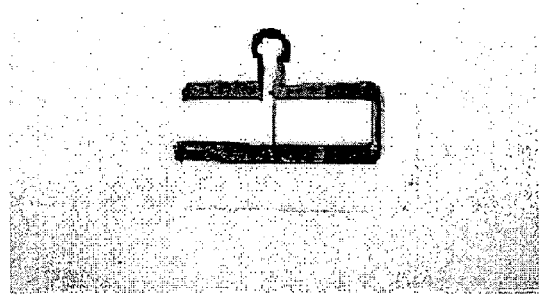
(B)
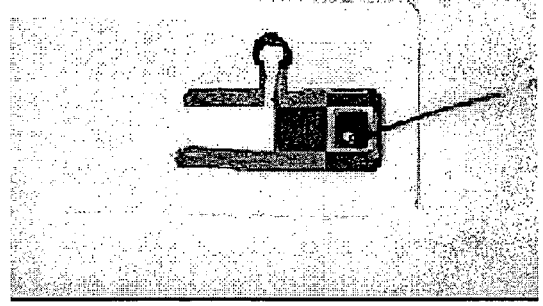
(C)
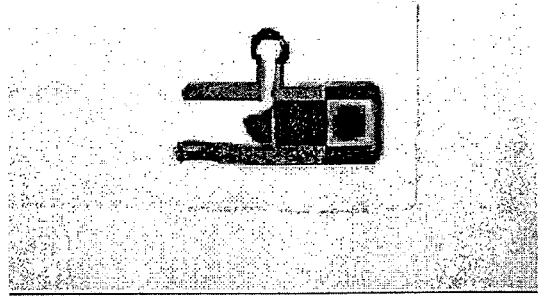
(D)
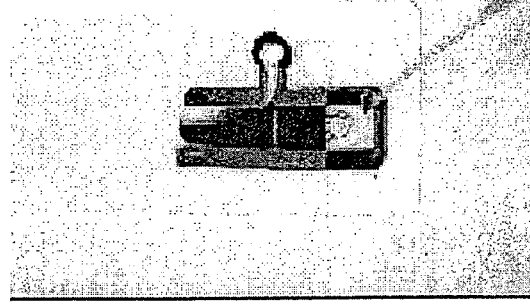

LIQUID SWITCH, AND MICROCHIP AND MASS-ANALYZING SYSTEM USING THE SAME

BACKGROUND OF THE INVENTION

1. Technical Field

The present invention relates to a liquid switch for controlling a liquid flow, and a microchip and a mass spectrometry system using thereof.

2. Background Art

In recent years, a micro-total analytical system (μ-TAS), in which chemical operations such as pre-processing, reaction, separating, detection or the like of a sample are conducted on a microchip, is rapidly developing. According to the micro-total analytical system, only a very small amount of a sample is required to be used, and analysis with higher sensitivity can be conducted with smaller environment load.

In patent literature 1, an apparatus for achieving a capillary electrophoresis by a micro channel-type chip having a configuration of being provided with a groove or a reservoir on a substrate is described. In this type of the microchip, it is critical to precisely control the timing for introducing a sample or a buffer solution into a channel in the chip. Such technique is requested not only in a separating apparatus and analysis apparatus, but also similarly in a micro chemical reactor.

Conventionally, control of the timing for introducing a sample is usually conducted by an application of an external force such as electric field, pressure and the like. However, such method is difficult to provide a precise control of a behavior of a very small amount of sample in the chip. Further, a problem of requiring larger size of the whole apparatus is also caused due to a necessity to provide an external force-applying unit.

Patent literature 1: Japanese Patent Laid-Open No. 2002-207,031

DISCLOSURE OF THE INVENTION

In view of the above-described circumstances, an object of the present invention is to provide a switch structure that can precisely control a fluidization of a liquid such as a sample or a buffer solution in a device such as microchip to conduct a separation, an analysis or a reaction of the sample with higher controllability under a desired condition. Further, another object of the present invention is to provide a switch structure that allows actuations of a plurality of production processes at an appropriate timing via a capillary force by one injection of the sample as a start, without a help of an external control unit.

According to one aspect of the present invention, there is provided a liquid switch, comprising: a channel for flowing a first liquid therethrough; a damming portion provided in the channel for damming the first liquid; and a trigger channel communicated into the channel at a position of the damming portion of downstream thereof and for guiding a second liquid to the damming portion.

In the liquid switch according to such aspect of the present invention, the aforementioned first liquid is dammed by the damming portion. A configuration, in which the damming portion absorbs first liquid and maintain the liquid, may be employed, or a configuration, in which the damming portion itself exhibits a lyophobicity for the first liquid and the first liquid is dammed at the upstream edge section thereof, may be employed. The liquid sample dammed at the damming portion is flowed out beyond the damming portion and toward the downstream thereof, when it comes into contact with the second liquid. According to the present invention, an opening of the channel can be achieved at a desired timing with higher controllability by introducing the second liquid, without providing an external control unit.

In the present invention, the damming portion may be configured to include a member for holding the first liquid. When such configuration is adopted, once the second liquid is introduced into the channel, liquid level of the first liquid maintained in the above-described member comes into contact with the liquid level of the second liquid. Then, the first liquid is flowed out beyond the damming portion toward the downstream thereof. As such, the opening of the channel can be achieved at a desired timing with higher controllability. The member holding the first liquid may be configured such that channel surface area per unit volume of the channel in the damming portion is larger than channel surface area per unit volume of the channel in other portions of the channel. This is because a capillary force is generated, so that a liquid-maintaining function is appeared. Specific examples of such structure include a plurality of particles, a porous member, a structure including a plurality of protruding portions that are separately arranged, or the like.

In the present invention, the damming portion may include a region exhibiting a lyophobicity for the first liquid. The region exhibiting the lyophobicity may be obtained by a method for forming the channel by employing a substrate exhibiting a lyophobicity for the first liquid and utilizing the surface thereof or by a method for processing the channel surface with such chemical compounds. By adjusting the degree of the lyophobicity, a smooth shifting to the opening status can be achieved, and further a smooth flow condition can be realized after achieving the opening status.

Here, a configuration further comprising a region exhibiting a lyophobicity for the first liquid at a downstream of an intersecting point in the channel where the channel intersects with the trigger channel may also be employed.

Having these configurations, the second liquid introduced from the trigger channel is maintained in a form of a band-shape, thereby allowing to provide a sample suitable for the separation of the components, for example.

In the present invention, a configuration may be employed, in which the liquid switch is configured to include a valve structure in the trigger channel, and wherein the valve structure is actuated once a specified quantity of the second liquid is introduced, to closedown the trigger channel. Having such configuration, just a specified quantity of the second liquid can be introduced therein.

Further, the second liquid introduced from the trigger channel is maintained in a form of a band-shape, thereby allowing to provide a sample suitable for separating components, for example. In particular, the introduction of the sample having the band-shape suitable for the separating operation can be stably achieved by simultaneously employing the aforementioned configuration comprising the lyophobic region at the downstream of the intersecting point in the channel where the channel intersects with the trigger channel.

According to another aspect of the present invention, there is provided a liquid switch, comprising: a channel for flowing a liquid therethrough; and a damming portion provided in the channel for damming the liquid; wherein the damming portion includes a member holding the liquid.

The switch can change its status to a switch-opening status by providing a vibration or by dropping a predetermined liquid material onto the damming portion. The member holding the liquid may be configured that a channel surface area per unit volume of the channel in the damming portion is larger than a channel surface area per unit volume of the channel in other portions of the channel. This is because a capillary force is generated, so that a liquid-maintaining function is appeared. Specific examples of such structure include a plurality of particles, a porous member, a plurality of protruding portions that are separately arranged or the like.

According to another aspect of the present invention, there is provided a liquid switch, comprising: a channel for flowing a liquid therethrough; and a damming portion provided in the channel for damming the liquid; wherein the damming portion includes a surface exhibiting a lyophobicity for the liquid.

The switch can change its status to a switch-opening status by providing a vibration or by dropping a predetermined liquid material onto the damming portion. The region exhibiting the lyophobicity may be obtained by a method for forming the channel by employing a substrate exhibiting a lyophobicity for the above-described liquid and utilizing the surface thereof or by a method for processing the channel surface with such chemical compounds. By adjusting the level of the lyophobicity, a smooth shifting to the opening status can be achieved, and further a smooth flow condition can be realized after achieving the opening status.

When the above-described configuration of providing the region exhibiting the lyophobicity is employed, the configuration may further comprise a moving member movably disposed between the damming portion and a place except the damming portion in the channel, wherein the liquid switch is configured that the moving member has a surface exhibiting a lyophilicity for the liquid, and that a position of the moving member can be adjusted from outside of the channel. In this case, when the moving member is located outside the region exhibiting the lyophobicity, the switch is in the status of closing. Once the moving member is located in the region exhibiting the lyophobicity, a passage along the surface of the moving member becomes to be a channel for the first liquid, so that the channel thereof is opened. Here, the configuration may further comprises a positioning unit that adjusts the position of the moving member from outside thereof, and one of the moving member and the positioning units, may be a magnet and the other maybe a magnetic material. Having such configuration, the location of the moving member can be adjusted from outside thereof.

According to further aspect of the present invention, there is provided a liquid switch, comprising: a channel for flowing a first liquid therethrough; a secondary channel communicating with the channel; a chamber communicating with the secondary channel; and a trigger channel communicating with the chamber and for introducing a second liquid into the chamber, wherein a lyophobic material exhibiting a lyophobicity for the first liquid is stored in an interior of the chamber, and wherein the liquid switch is configured that the lyophobic material is introduced from the chamber into the channel once the second liquid is introduced from the trigger channel into the chamber.

The liquid switch may be further configured that the chamber comprises: a first compartment communicating with the secondary channel; a second compartment for storing the lyophobic material; and a separating portion disposed between the first compartment and the second compartment for separating the compartments, and the trigger channel communicates with the separating portion, and the liquid switch may be configured that the lyophobic material moves from the first compartment to the second compartment once the second liquid is introduced from the trigger channel. In this case, the second compartment that stores the lyophobic material may preferably be configured to have no communication with the secondary channel. The lyophobic material may be a liquid or a gas, or air and the like. This liquid switch is configured so that a lyophobic material is introduced into the first liquid channel by introducing the trigger of the second liquid as a start to close the channel. According to the present invention, fluidization of the liquid in the channel can be certainly stopped with a simple structure.

According to yet other aspect of the present invention, there is provided a microchip, comprising: a substrate; a sample channel formed on the substrate for passing a sample therethrough; and sample separating portion provided in the sample channel, wherein the liquid switch is disposed in the sample channel, and a feeding of the sample from the sample channel to the sample separating portion is controlled with the liquid switch.

According to yet other aspect of the present invention, there is provided a microchip, comprising: a substrate, a liquid channel formed on the substrate for flowing a liquid therethrough; and a reaction portion provided in the liquid channels, wherein the liquid switch is disposed in the liquid channel, and a feeding of the liquid from the liquid channel to the reaction portion is controlled with the liquid switch.

The microchip may further comprises a reservoir communicating with the reaction portion for being introduced with an agent, and the liquid switch may be disposed in a liquid channel extending from the reservoir to the reaction portion, and an introduction of the agent from the reservoir into the reaction portion may be controlled with the liquid switch. The agent may be, for example, an enzymatic digestion solution such as a tryptic digestion solution.

According to yet other aspect of the present invention, there is provided a microchip, comprising: a substrate, a principal channel formed on the substrate for flowing a liquid therethrough; a clock channel for controlling a timing of the liquid passing a predetermined point in the principal channel; and a control channel communicating with the principal channel and the clock channel, wherein the liquid switch is disposed in the control channel, and a transfer of the liquid in the principal channel is controlled with the liquid switch.

According to the present invention, various processing conducted on the chip such as separating operation, reaction or the like can be accomplished with higher time controllability by utilizing the clock channel.

In these microchips, the separation and the reaction of the sample can be conducted under a desired condition with higher controllability by utilizing the liquid switch. In particular, according to the configuration being provided with the clock line, mixing, reaction, separating or the like of the liquid can be conducted at an appropriate timing according to a predetermined schedule.

According to yet other aspect of the present invention, there is provided a mass spectrometry system, comprising: a separating unit that separates biological sample according to molecular size or a property thereof; a pre-processing unit that conducts a pre-processing including an enzymatic digestion processing for the sample separated by the separating unit; a drying unit that dries the preprocessed sample; and a mass spectrometry unit that conducts mass spectrometry of the dried sample, wherein the separating unit includes the above-described microchip.

According to yet other aspect of the present invention, there is provided a mass spectrometry system, comprising:

a separating unit that separates biological sample according to molecular size or a property thereof; a pre-processing unit that conducts a pre-processing including an enzymatic digestion processing for the sample separated by the separating unit; a drying unit that dries the preprocessed sample; and a mass spectrometry unit that conducts mass spectrometry of the dried sample, wherein the pre-processing unit includes the above-described microchip.

According to yet other aspect of the present invention, there is provided a mass spectrometry system, comprising: a separating unit that separates biological sample according to molecular size or a property thereof; a pre-processing unit that conducts a pre-processing including an enzymatic digestion processing for the sample separated by the separating unit; a drying unit that dries the preprocessed sample; and a mass spectrometry unit that conducts mass spectrometry of the dried sample, where the separating unit, the pre-processing unit or the drying unit includes the above-described microchip.

According to these mass spectrometry systems, a sample suitable for the mass spectrometry can be prepared with higher efficiency.

As have been described above, according to the present invention, the switch structure for precisely controlling the fluidization of the liquid such as the sample or the buffer in the device such as microchip to conduct the separation, the analysis or the reaction of the sample with higher controllability under the desired condition can be presented.

BRIEF DESCRIPTION OF THE DRAWINGS

The above and other objects, features and advantages of the present invention will be more apparent from the following description and the annexed drawings, in which:

FIG. 4 is a diagram, illustrating the switch structure according to the embodiment;

FIG. 11 is a diagram, illustrating a switch structure according to the embodiment;

FIG. 12 is a diagram, illustrating a switch structure according to the embodiment;

FIG. 14 is a diagram, illustrating a chip structure according to the embodiment;

FIG. 15 is a diagram, illustrating a switch structure according to the embodiment;

FIG. 18 is a diagram, illustrating a switch structure according to the embodiment;

FIG. 21 is a diagram, illustrating a switch structure according to an example;

FIG. 22 is a diagram, illustrating a switch operation according to an example;

BEST MODE FOR CARRYING OUT THE INVENTION

Embodiments of the present invention will be described as follows, in reference to the annexed drawings. Switches described in respective embodiments are employed for controlling a liquid that is transported through a channel in a microchip having a configuration comprising a channel or a reservoir on a substrate.

It is assumed in the following description that the introduced liquid is an aqueous solution unless otherwise instructed. In addition, while a quartz substrate is employed as a substrate in each of the following embodiments, other material such as plastic material, silicon or the like may also be used. The plastic materials include, for example, thermoplastic resins such as silicone resins, polymethyl methacrylate (PMMA), polyethylene terephthalate (PET), polycarbonate (PC) and the like, or thermosetting resins such as epoxy resins and the like. These materials can be easily formed and processed, and thus manufacturing cost can be reduced. In addition, while the method for forming a portion such as the channel or the reservoir in the microchip includes a combined method of a photolithography with an etching, when a plastic material is employed as a substrate material, an injection molding, a hot embossing or the like may also be employed.

Further, while the apparatus including the channel, in which the liquid moves by the capillary force, is illustrated in the following embodiments, other configurations that provides a movement of a liquid by utilizing an external force such as pumping, electric field, attractive force and the like may also be employed.

First Embodiment

In the present embodiment, an example of a liquid switch comprising a member for holding a liquid, which is disposed in a sample damming portion, will be illustrated. This liquid switch can be manufactured by forming a trench on a surface of a quartz substrate. Since the surface of the quartz substrate is hydrophilic, the inner walls of the trench are also hydrophilic surfaces. The apparatus including such switch is free of any external force-applying units such as pump or electric field, and the liquid moves through the channel by the capillary force.

Figure 1:
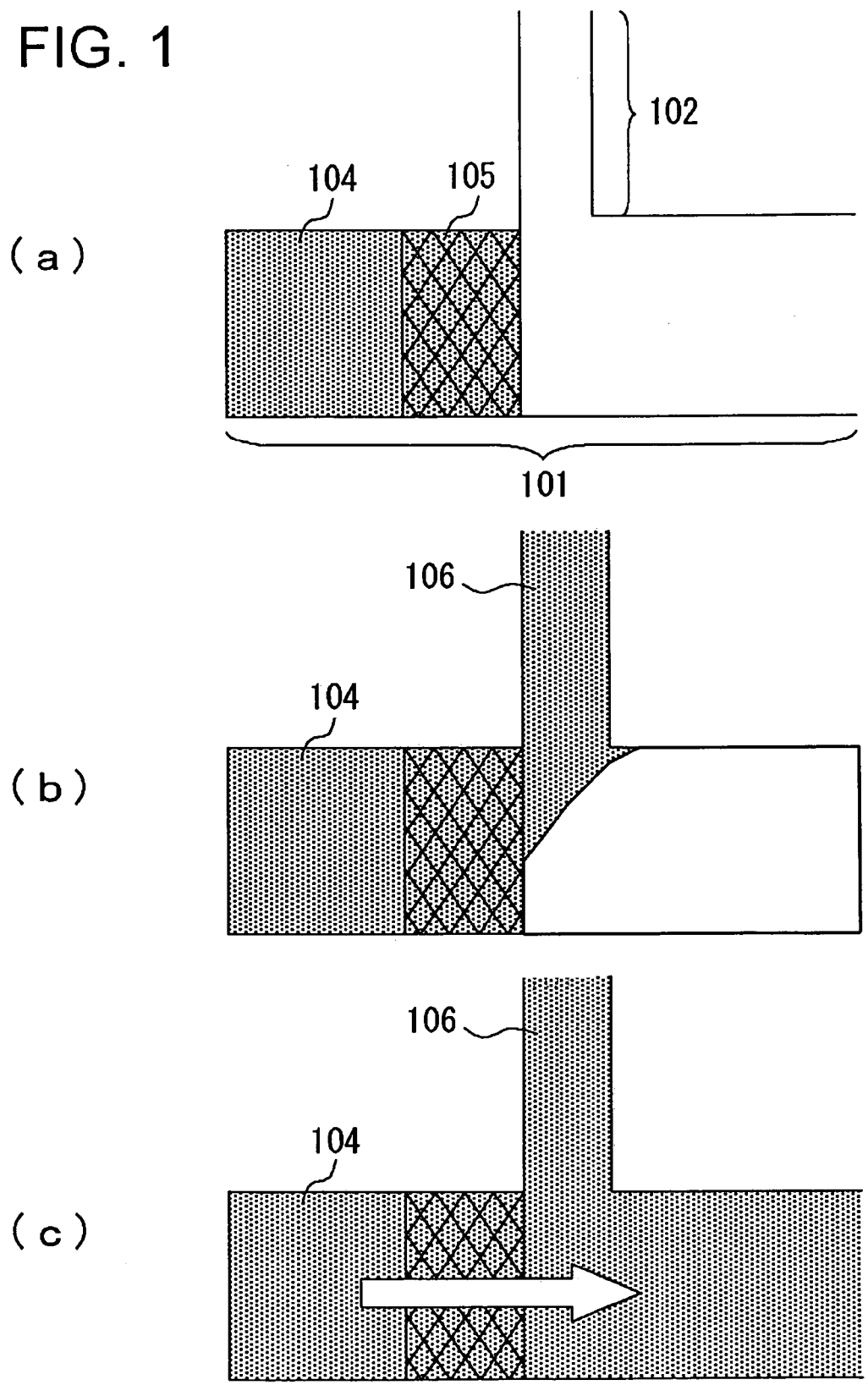
FIGS. 1(a), 1(b) and 1(c) are diagrams, illustrating a switch structure according to the embodiment.

FIGS. 1(a), 1(b) and 1(c) are plan views of the liquid switch, and more specifically, FIG. 1(a) shows a closing status of the switch, and FIGS. 1(b) and 1(c) show an opening status of the switch. In these figures, a trigger channel 102 is connected to a side surface of a principal channel 101. The trigger channel 102 is capable of adjusting a liquid transferring velocity in the channel by suitably adjusting the degree of the hydrophilicity in the channel or a diameter of the channel. This provides a control of a rate of the switching operation. A damming portion 105 is provided in an upstream of an intersecting region of the principal channel 101 with the trigger channel 102. (left side in the figure) Damming portion 105 is a portion having stronger capillary force than other portions in the channel. A specific configuration of the damming portion 105 may be illustrated as follows.

(i) Configuration Being Provided with a Plurality of Columnar Members

In this configuration, a channel surface area per channel unit volume in the damming portion 105 is larger than that of other portions of the channel. In other words, when the principal channel 101 is filled with a liquid, the surface area thereof in the damming portion 105 in the channel is larger than other portions in the channel, and thereby providing larger solid-fluid interface.

(ii) Configuration Being Filled with a Plurality of Porous Members or Beads

In this configuration, it is configured that the surface area of the damming portion 105 in the channel is larger than other portions thereof, so that larger solid-fluid interface is presented.

When the above-described configuration (i) is employed, the columnar members can be formed via a suitable method corresponding to the type of the substrate. When a quartz substrate is employed, they can be formed by utilizing a photolithography technique and a dry etching technique. When a plastic plate is employed, a desired patterned surface for the columnar members can be obtained by manufacturing a metal mold having a reverse pattern of the columnar member pattern to be formed and conducting the molding using thus manufactured metal mold. Here, such metal mold can be formed by utilizing a photolithography technique and a dry etching technique.

When the above-described configuration (ii) is employed, a predetermined point of the channel can be directly filled with the porous members and/or the beads, or the porous members and/or the beads can be directly adhered to a predetermined point of the channel.

In the present embodiment, the above-described configuration (i) is employed.

Figure 2:
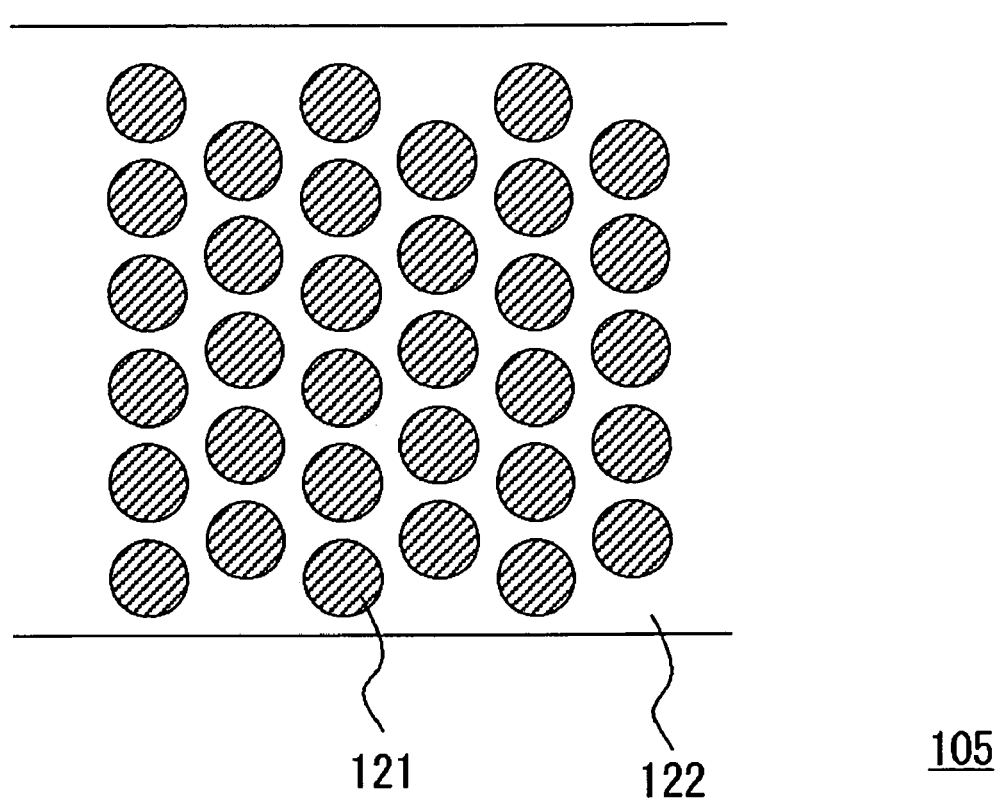
FIG. 2 is a diagram, illustrating a structure of a damming portion included in the switch structure according to the embodiment.

FIG. 2 is a plan view of the damming portion 105. A plurality of columnar members 121 are arranged with substantially regular intervals. Other regions except the columnar member 121 function as micro channels 122. The surface area of the channel per unit volume of the channel in the damming portion 105 is larger than that of other portions in the channel. Thus, the liquid entering into the damming portion 105 is sustained in the micro channels 122 by the capillary force.

FIG. 1(a) illustrates a liquid switch in the status of the standby. The liquid sample 104 introduced into the principal channel 101 is sustained in the damming portion 105. When the trigger solution 106 is introduced at a desired timing under such condition, a tip portion of the liquid level of the trigger solution 106 proceeds forward, thereby coming into contact with the damming portion 105, as shown in FIG. 1(b). While the liquid sample 104 is maintained in the damming portion 105 by the capillary force when it is in the condition shown in FIG. 1(a), once the liquid sample 104 is in the condition of coming into contact with the trigger solution 106 as shown in FIG. 1(b), the liquid sample 104 moves toward the right direction in figure (i.e., toward the downstream), and then the liquid sample 104 flows out to the downstream of the principal channel 101 shown in FIG. 1(c). More specifically, the trigger solution 106 functions as priming, thereby appearing the operation as the liquid switch.

Figure 3:
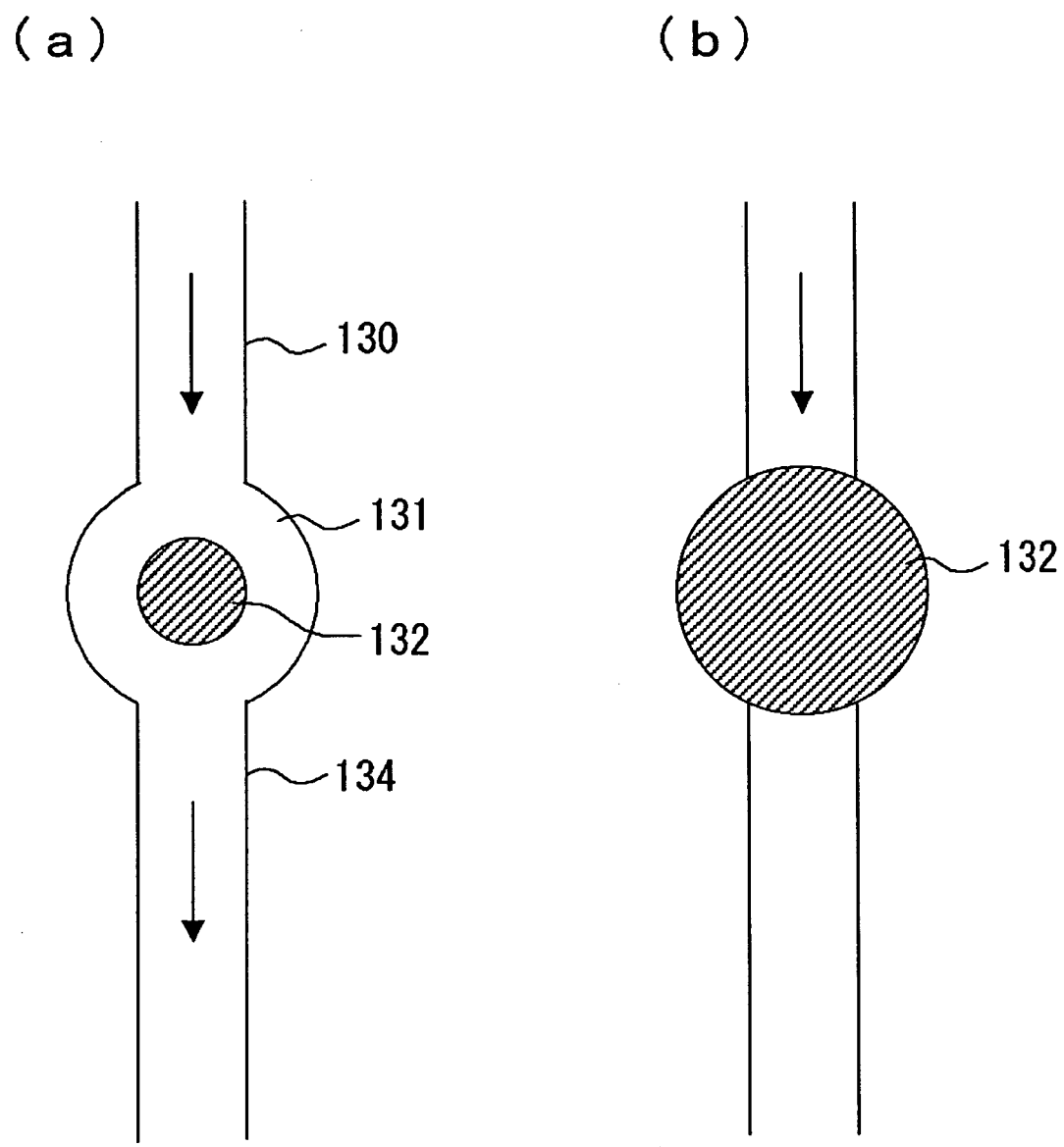
FIG. 3 is a diagram, illustrating a valve structure for holding a trigger solution in the switch structure according to the embodiment.

In the switch described above, when the switch is in the opening status, the trigger solution 106 is continually supplied to the principal channel 101. However, there may be a case that it is necessary to minimize the mixing of the trigger solution 106 into the principal channel 101, depending on the object for providing the switch. Although such control is generally difficult, such control can certainly be carried out by employing a valve construction shown in FIGS. 3(a) and 3(b), for example. In the valve construction shown in FIG. 3(a), a liquid sample inflow path 130, a chamber 131 and a liquid sample drain path 134 are provided in this order from the upstream of the channel toward the downstream thereof. Water absorption gel 132 is disposed in the chamber 131. Water absorption gel 132 is configured to expand its volume when the gel contacts the liquid flowed therein, filling the space of the chamber 131 therewith. FIG. 3(b) is a diagram, illustrating a status, in which the trigger solution is introduced into the chamber 131 and the water absorption gel 132 expands therein. In this status, the fluid introduced from the upstream of the liquid sample inflow path 130 is no longer allowed to flow out to the downstream of the chamber 131. In other words, the water absorption gel 132 functions as the damming portion material.

Second Embodiment

The present embodiment relates to a switch construction employing a hydrophobic region as a damming portion material. The liquid switch can be manufactured by forming a trench on a surface of a quartz substrate. Since the quartz substrate is employed, the inner walls of the trench are hydrophilic surfaces. The hydrophobic region is obtained by hydrophobic-processing a lid portion having a quartz glass surface.

In this switch, a trigger channel 102 is coupled to a side surface of a principal channel 101 as shown in FIG. 4(a), and an upstream of an intersecting portion thereof in the principal channel 101 is provided with a damming portion 110 composed of a hydrophobic region. The principal channel 101 and the trigger channel 102 except the damming portion 110 composed of the hydrophobic region are hydrophilic regions. The selective preparations of the hydrophilic region and the hydrophobic region are conducted as follows in the present embodiment. More specifically, after providing a coating member covering the upper surface of the channel over the whole channel of the principal channel 101, a sample-contacting surface of the coating member is processed to provide a hydrophobicity in the damming portion 110 and to provide a hydrophilicity in other regions. A cross-sectional view of the channel shown in FIG. 4(a) is a diagram for describing such status. In the cross-sectional view of the left side, the coating member composed of a quartz glass is employed as it is, and in the cross-sectional view of the right side, a silazane-processed coating member is disposed to take the silazane-processed surface in the inside. When the liquid sample 104 is introduced from the upstream of the principal channel 101 (left side in the figure) for this switch construction, the liquid level moves to the middle of the damming portion 110.

In such status, when the trigger solution 106 is further introduced at a desired timing, the tip of the liquid level of the trigger solution 106 enters into the damming portion 110, contacting with the tip of the liquid level of the liquid sample 104 (FIG. 4(b)). Then, the liquid sample 104, which has been maintained heretofore by the damming portion 110, starts to fluidize by a driving force exerting toward the downstream in the right side in the figure. As such, the switching operation of the fluidization of the liquid sample 104 by the introduction of the trigger solution 106 is achieved.

In this embodiment, in FIG. 4(b), it is critical to maintain the tip of the liquid level of the liquid sample 104 staying within the region of the damming portion 110 composed of the hydrophobic region and to provide a smooth fluidization of the liquid sample 104 once the trigger solution 106 is introduced. In order to achieve these conditions, it is desirable to appropriately control the hydrophobicity of the damming portion 110. Methods for achieving the status includes, for example, selection or quantitative optimization of the material for the hydrophobic-processing of the damming portion 110, and besides these, preferable design of the structure of the channel may also be employed to achieve the status.

Figure 5:
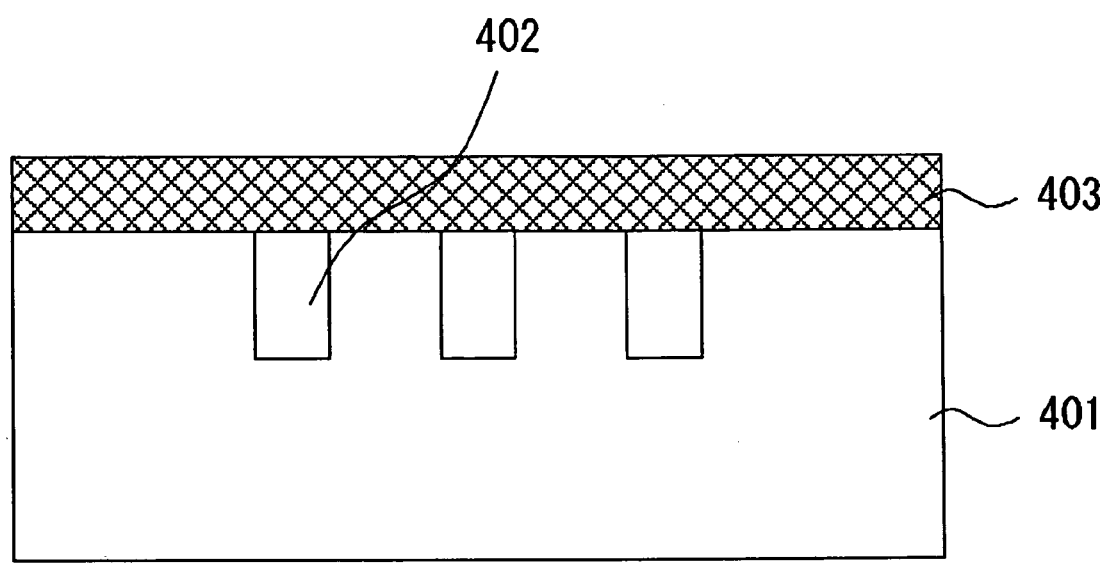
FIG. 5 is a diagram, illustrating a cross section structure of the switch according to the embodiment.

FIG. 5 is an example of a structure for providing such control of the hydrophobicity. FIG. 5 is a cross-sectional view of the damming portion 110 shown in FIG. 4(a). A plurality of micro channels 402 are provided in the substrate 401, and the upper surface thereof is coated with a coating material 403. Micro channels 402 have hydrophilic surfaces, and the coating material 403 has a hydrophobic-processed surface by a silazane processing. Since a plurality of micro channels 402 are provided in this structure, an appropriate water retentivity is maintained by a capillary force, and on the other hand, a hydrophobicity is also provided to the coating material 403 of the upper surface of the channel. In this structure, the liquid holding ability is determined by suitably balancing between the water retentivity presented by the capillary force and the hydrophobicity of the channel. Further in this structure, percentage of a ratio of the hydrophobicity surface and the hydrophilic surface can be freely controlled by controlling the number or the width of the micro channels 402, and as a result, the hydrophobicity as the whole can be controlled to provide a desired value. The level of the hydrophobicity can be suitably controlled by controlling such structure or controlling the surface condition thereof.

The hydrophobic processing in the present embodiment can be achieved by adhering or combining onto the substrate surface a chemical compound having a chemical structure containing an unit being adsorbed or chemically-bound to the substrate material and an unit having hydrophobic-modified group in molecular. Silane coupling agent, for example, may be used as such type of chemical compound.

Preferable silane coupling agent having hydrophobic group may include compounds having silazane bond group such as hexamethyldisilazane and compound having thiol group such as 3-thiol propyl triethoxysilane.

Available coating methods of the coupling agent solution may include spin coating, spraying, dipping, vapor processing and the like. The spin coating is a method for applying a liquid containing a material composing a binding layer dissolved or dispersed therein such as coupling agent and the like by using a spin coating machine. This method provides better film thickness controllability. The spraying is a method for spraying a coupling agent solution or the like toward the substrate, and the dipping is a method for dipping the substrate within a coupling agent solution or the like. According to these methods, the film can be formed with simple and easy process without a need for any particular apparatus. The vapor processing is a method, in which the substrate is heated as required and vapor of a coupling agent solution or the like is flowed thereon. This method also provides a formation of a thin film with better film thickness controllability. Among these, the method for spin-coating a silane coupling agent solution is preferably employed. This is because better adhesion is stably obtained. At this stage, the silane coupling agent concentration in the solution may preferably be 0.01 to 5% v/v, and more preferably be 0.05 to 1% v/v. Available solvent for the silane coupling agent solution may include, alone or a combination of two or more of: pure water; alcohols such as methanol, ethanol, isopropanol and the like; esters such as ethyl acetate; and the like. Among these, ethanol, methanol or ethyl acetate, diluted with pure water, are preferable. This is because particularly considerable effect of improvement in the adhesion can be obtained. After applying the coupling agent solution or the like, drying is conducted. While the drying temperature is not particularly limited, the operation is usually conducted at a range of from a room temperature (25 degree C.) to 170 degree C. Drying time depends on temperature, but is usually 0.5 to 24 hours. Drying may be conducted in the air, or drying may be conducted in an inert gas such as nitrogen and the like. For example, a nitrogen blow method, in which drying is conducted while spraying nitrogen on the substrate, can be employed. Further, as a method for manufacturing the coupling agent film, a film composing of a silane coupling agent is formed over the entire surface of the substrate by Czochralski method for Langmuir-Blodgett film (LB film), as described in "NATURE, vol. 403, 13, January (2000)", to form a micro pattern of hydrophilic/hydrophobic portions.

Further, the hydrophobic processing can be conducted by using a printing technique such as stamping or ink-jet. In the method of utilizing the stamping, polydimethylsiloxane (PDMS) resin is typically employed. Resinification of PDMS resin can be conducted by polymerizing a silicone oil, and after the resinification, a status of being filled with the silicone oil in molecular gaps is attained. Thus, when the PDMS resin is in contact with a hydrophilic surface such as, for example, a glass surface, the contact portion exhibits strong hydrophobicity, thereby repelling water. This phenomenon is utilized to easily prepare the aforementioned hydrophobic-processed channel by contacting the hydrophilic substrate using a PDMS block having a concave portion formed in a position corresponding to the channel portion as a stamp.

In the method by utilizing the ink-jet printing, similar advantageous effect can be obtained by typically employing a silicone oil having lower viscousness as an ink of the ink-jet printing and carrying out a printing to provide a pattern that promote an adhesion of the silicone oil on the channel wall.

Third Embodiment

Figure 6:
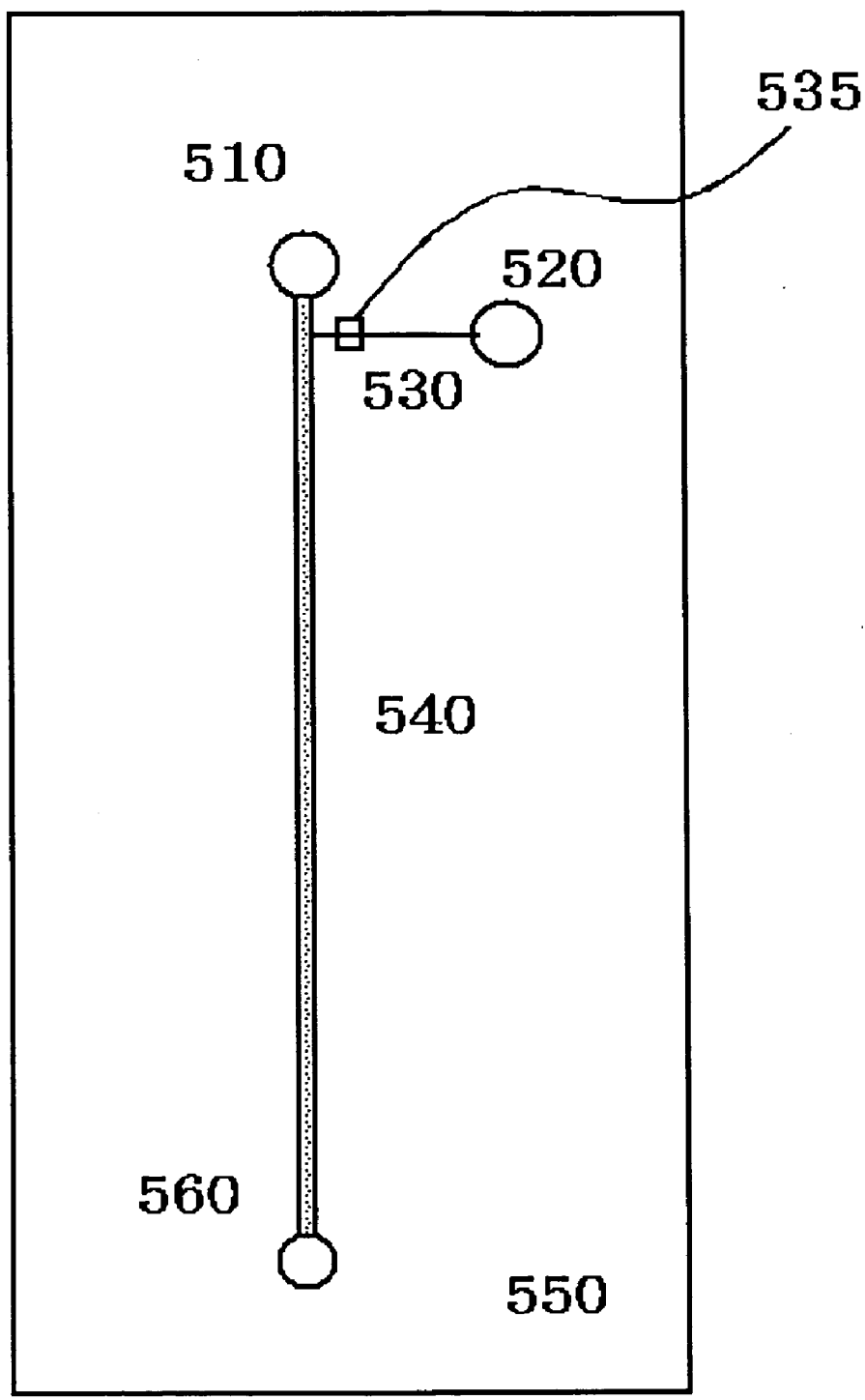
FIG. 6 is a diagram, illustrating a structure of a separating apparatus according to the embodiment.

FIG. 6 is a diagram, illustrating an example of a separating apparatus employing a liquid switch in a sample inlet. This separating apparatus utilizes a capillary phenomenon for moving a sample to conduct a separation of the sample according to molecular size by using a channel for separation 540. The apparatus eliminates a need for applying an external force such as electric power, pressure or the like, and also eliminates a need for a driving energy. The separating apparatus has a configuration, in which a channel for separation 540 is provided on a substrate 550. One end of the channel for separation 540 is provided with an air opening 560, and the other end is provided with a buffer injection port 510 for injecting a buffer. The channel for separation 540 is tightly sealed except portions of the buffer injection port 510 and the air opening 560. A sample quantification tube 530 is connected to a beginning of the channel for separation 540, and the other end of the sample quantification pipe 530 is provided with a sample injection port 520. In the sample quantification tube 530, a stop valve 535 is provided in a portion just before a point thereof intersecting with the channel for separation 540. The structure of the stop valve 535 is similar to that described in FIG. 3 and the related descriptions thereof.

In operating such apparatus, a buffer has been introduced into the channel for separation 540 through the buffer injection port 510 in advance.

FIGS. 7(a) to 7(c) are magnified views of a vicinity of an intersecting point of the sample quantification tube 530 and the channel for separation 540. A liquid switch is formed in this portion. FIGS. 7(a) to 7(c) are plan views of such liquid switch, and more specifically FIG. 7A shows a switch closing status, and FIGS. 7(b) and (c) show a switch opening status. In these diagrams, the sample quantification tube 530 is connected to the side surface of the channel for separation 540. Damming portions 110 are disposed in both of the upstream and the downstream of an intersecting region of the channel for separation 540 and the sample quantification tube 530. In the downstream of the intersecting region, a separating portion 113 is formed adjacent to the damming portion 110. The separating portion 113 is filed with silica gel powder for separating the sample. Filling process into the channel for separation 540 with the silica gel powder can be conducted by, after providing a damming portion material in the downstream thereof, in pouring a mixture of the silica gel powder, a binder and water into the channel for separation 540, and thereafter drying and caking the mixture, and thus the above-described structure is obtained.

In the sample quantification tube 530 functioning as a trigger channel, a chamber 131 is provided. In the chamber 131, water absorption gel 132 is disposed. An water-insoluble water absorption polymer is preferably employed for the water absorption gel 132, and it is configured that the gel expands their volume when the gel contacts a liquid flowed therein to fill up the space of the chamber 131 therewith.

Figure 7:
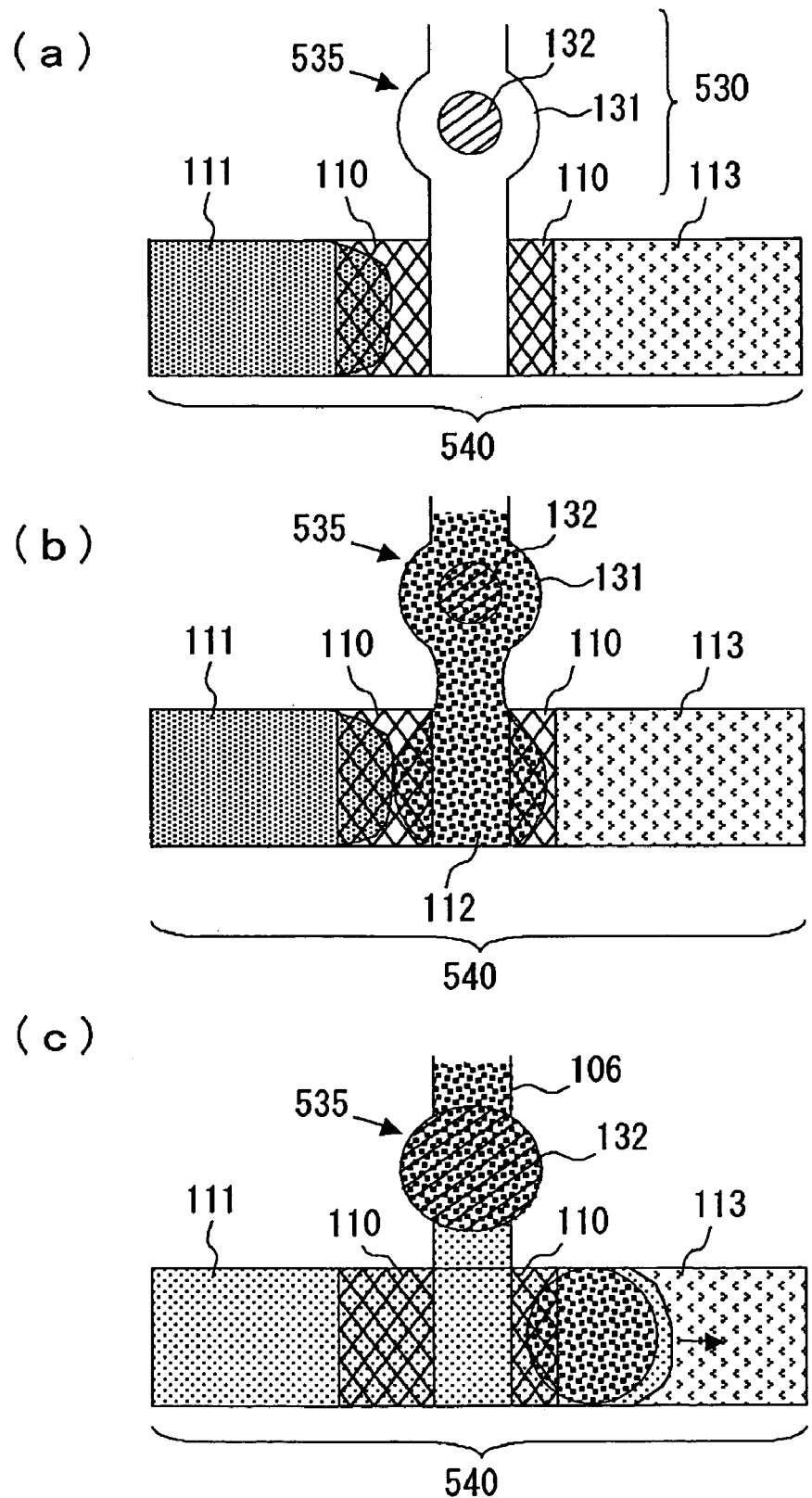
FIG. 7 is a diagram, illustrating a switch structure according to the embodiment.
Figure 8:
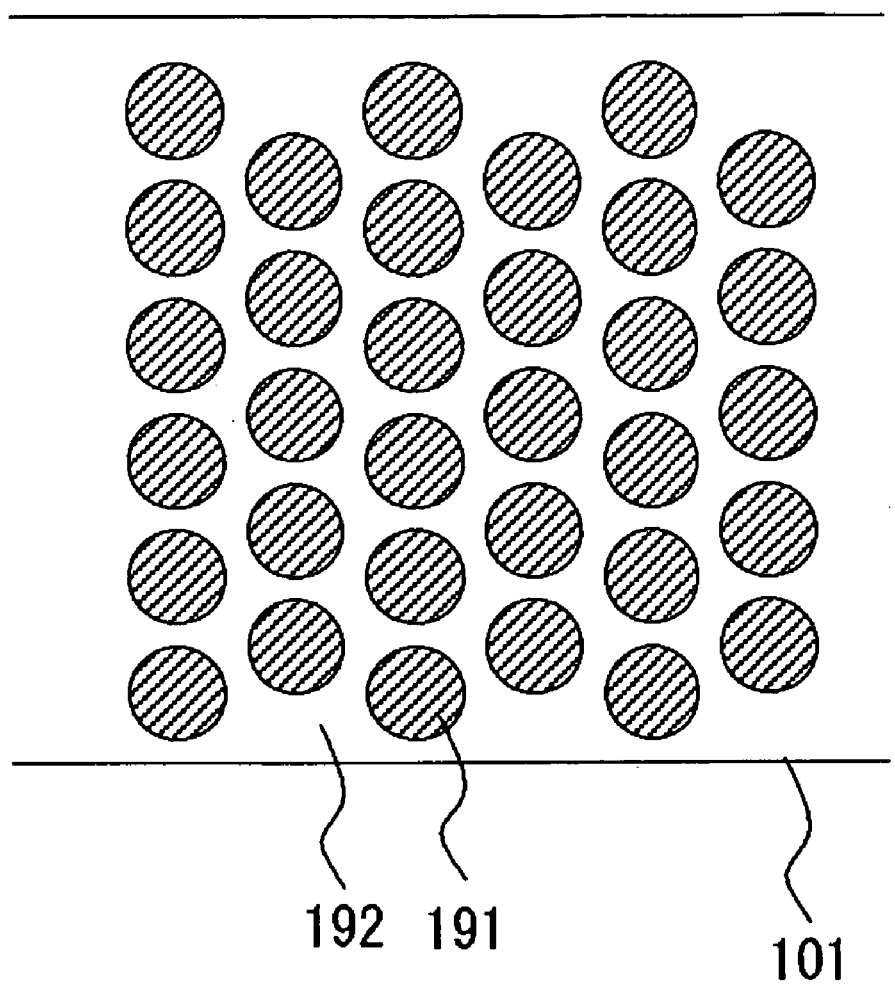
FIG. 8 is a diagram, illustrating a structure of the damming portion included in the switch structure according to the embodiment.

FIG. 8 is a plan view of the damming portion 110 of FIG. 7. A plurality of hydrophobic regions 191 are regularly disposed at substantially same intervals. The surface of the quartz substrate is exposed in the other regions than the hydrophobic region 191 to form hydrophilic regions 192. The hydrophobicity of the damming portion 110 is suitably controlled by forming such hydrophobic/hydrophilic pattern. As a result, in FIG. 7(a), the tip of the liquid level of the buffer 111 stays in the hydrophobic region 105, and once the trigger solution is introduced, the buffer 111 smoothly flows toward the downstream.

Returning to FIGS. 7(a) to 7(c), FIG. 7(a) illustrates the liquid switch in a standby status. The buffer 111 introduced into the channel for separation 540 is dammed in the damming portion 110.

Under such status, when the sample 112 functioning as the trigger solution is introduced at a desired timing, the tip portion of the liquid level of the sample 112 proceeds as shown in FIG. 7(b), thereby coming into contact with the damming portion 110. Although the buffer 111 remains in the damming portion 110 in the status shown in FIG. 7(a), the buffer 111 begins to move toward the right direction in the figure (downstream), when the buffer 111 is in a status shown in FIG. 7(b), in which the buffer contacts the sample 112.

In such occasion, once the sample 112 is introduced into the sample quantification tube 530 functioning as the trigger channel, the water absorption gel 132 expands to fully occupy the interior of the chamber 131. Having this configuration, the sample 112 is in a status that the flow out thereof toward the downstream of the chamber 131 is no longer allowed. In other words, the water absorption gel 132 functions as the damming portion material.

A specified quantity of the sample 112 is introduced into the channel for separation 540 by this effect, and subsequently, as shown in FIG. 7(c), the sample 112 is guided to the separating portion 113, where the separating operation of the component contained in the sample is conducted.

As described above, the sample is smoothly introduced into the separating apparatus shown in FIG. 6.

Fourth Embodiment

Figure 9:
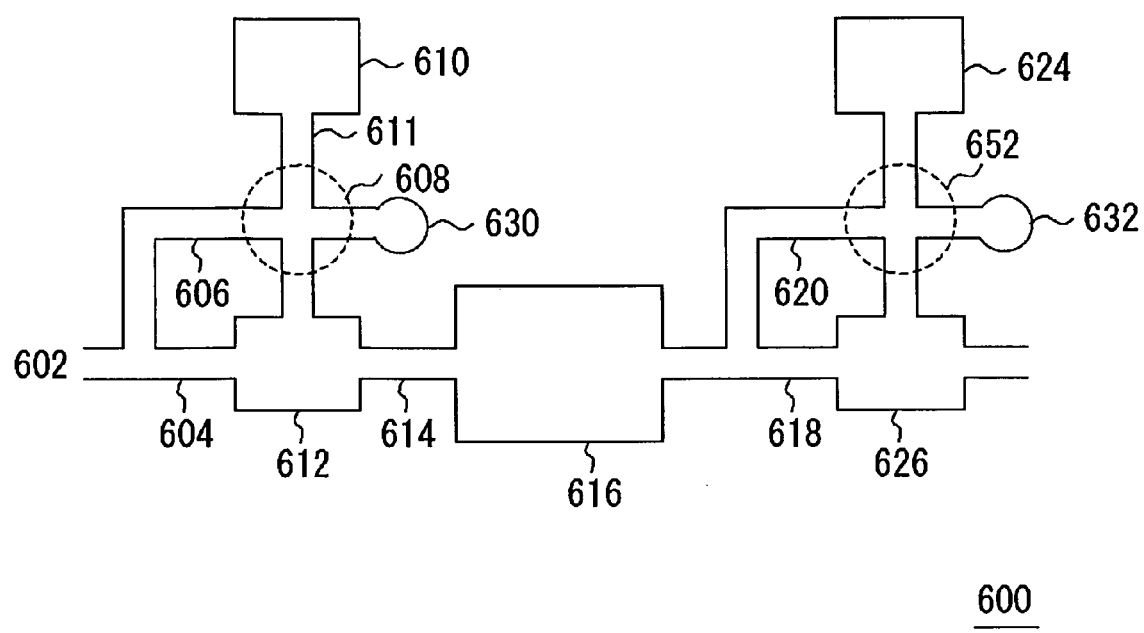
FIG. 9 is a diagram, illustrating a structure of a micro chemical reactor according to the embodiment.

FIG. 9 illustrates an example of a micro chemical reactor employing a liquid switch. This apparatus is composed of channel grooves formed on a quartz substrate by a dry etching, a reservoir for storing a reacting solution and a reaction chamber. This apparatus is configured that a sample and a reagent are mixed by a predetermined time schedule so that the reaction sequentially proceeds. A embodiment of conducting a trypsinization for a protein by using such apparatus to prepare a sample for Matrix-Assisted Laser Desorption Ionization-Time of Flight Mass Spectrometer (MALDI-TOFMS) will be described as follows.

In this apparatus, channels and the like having the illustrated forms are formed on the surface of the quartz substrate. This apparatus is free of any external force-applying unit such as a pump and an electric field, and a liquid will proceeds through the channel by a capillary force.

A sample 602 containing protein introduced into a solution mixing equipment 600 is branched into a channel 604 and a channel 606 and both are respectively fluidized, and one is led to a reservoir 612 and the other is led to a switch 608. Detailed structure of the switch 608 is a structure shown in FIG. 4, the principal channel 101 in FIG. 4 corresponds to the channel 611 of FIG. 9, and the trigger channel 102 in FIG. 4 corresponds to the channel 606 of FIG. 9. An inflow of the sample 602 functions as a trigger, thereby providing "opening" status for the switch 608.

A tryptic digestion solution is stored in a solution tank 610, and the liquid level thereof is maintained to be higher than the liquid level within the channel provided for such apparatus. It is designed that the tryptic digestion solution is accumulated in this portion when the switch 608 is in a "closing" status. When the channel is in the "opening" status, the tryptic digestion solution is transported to the downstream of the channel 611 (toward the bottom side in the figure). As a result, the tryptic digestion solution is guided to the reservoir 612, where this is mixed with the sample 602 containing the protein. The liquid mixture is guided from the reservoir 612 through the channel 614 to the chamber 616. Here, a chamber 630 comprising an opening is provided at an end of the channel 606.

The chamber 616 is designed to have larger volume, and functions as a time delay element. More specifically, the liquid mixture of the sample 602 containing the protein and the tryptic digestion solution is continuously supplied into the chamber 616 until the interior of the chamber is filled up, and once the chamber 616 is fully filled, the liquid mixture overflows and is flowed toward the downstream. Since the switch 608 maintains its status of "open," the tryptic digestion solution is continually supplied from the solution tank 610, and the sample 602 is also sequentially introduced therein. As a result, the quantity of the liquid within the chamber 616 is gradually increased, and eventually exceeds the capacity at a time hour, and then is transported toward the downstream. A certain time passes till the chamber 616 is fully filled, and meanwhile the trypsinization of the sample 602 containing the protein is carried out at a temperature of 37 degree C. Here, pH of the trypsinized liquid is on the order of 7.6.

The overflowed trypsinized solution is branched to the channel 618 and the channel 620 and flowed out therethrough. The trypsinized compound guided to the channel 620 functions as a trigger for the switch 652, so that the switch 608 is turned to "open." Here, a chamber 632 comprising an opening is provided at an end of the channel 652.

6N—HCl is stored in the solution tank 624, and the liquid level thereof is maintained to be higher than the liquid level within the channel provided to such apparatus. 6N—HCl stays in this portion when the switch 652 is in a "closed" status. When the channel is in the "opening" status, 6N—HCl is transported toward the downstream (toward the bottom side in the figure).

As a result, 6N—HCl is guided to the reservoir 626, where this is mixed with the trypsinized solution. This reduces pH of the trypsinized solution, thereby stopping the reaction of the trypsinized solution. Here the purpose for reducing pH is not limited to the stopping of the reaction, but achieving the preferable condition for preparing the sample for measurement by mixing a matrix employed in the MALDI-TOFMS.

As above described, the trypsinization is conducted on the microchip at a designed timing. Reaction time by the tryptic digestion solution can be controlled by adjusting the volume of the chamber 616 or the like.

In the present embodiment, it is critical to adjust the timing for introducing the sample 602 into the reservoirs 612 and 626 and the timing for introducing the tryptic digestion solution and/or the stopping solution therein. In the present embodiment, suitable adjustment thereof can be achieved by a suitable design of these reservoirs and/or the solution tanks 610 and 624, or the channel 611.

Fifth Embodiment

In the present embodiment, a plurality of switch structures are provided to an apparatus comprising a combination of an ultrafiltration apparatus and a separating apparatus. A switch structure is employed, so that an introduction and a fluidization of a sample is automatically conducted. Since any pump or electric charge application unit for providing an external force is not required, the whole apparatus can be miniaturized.

Figure 10:
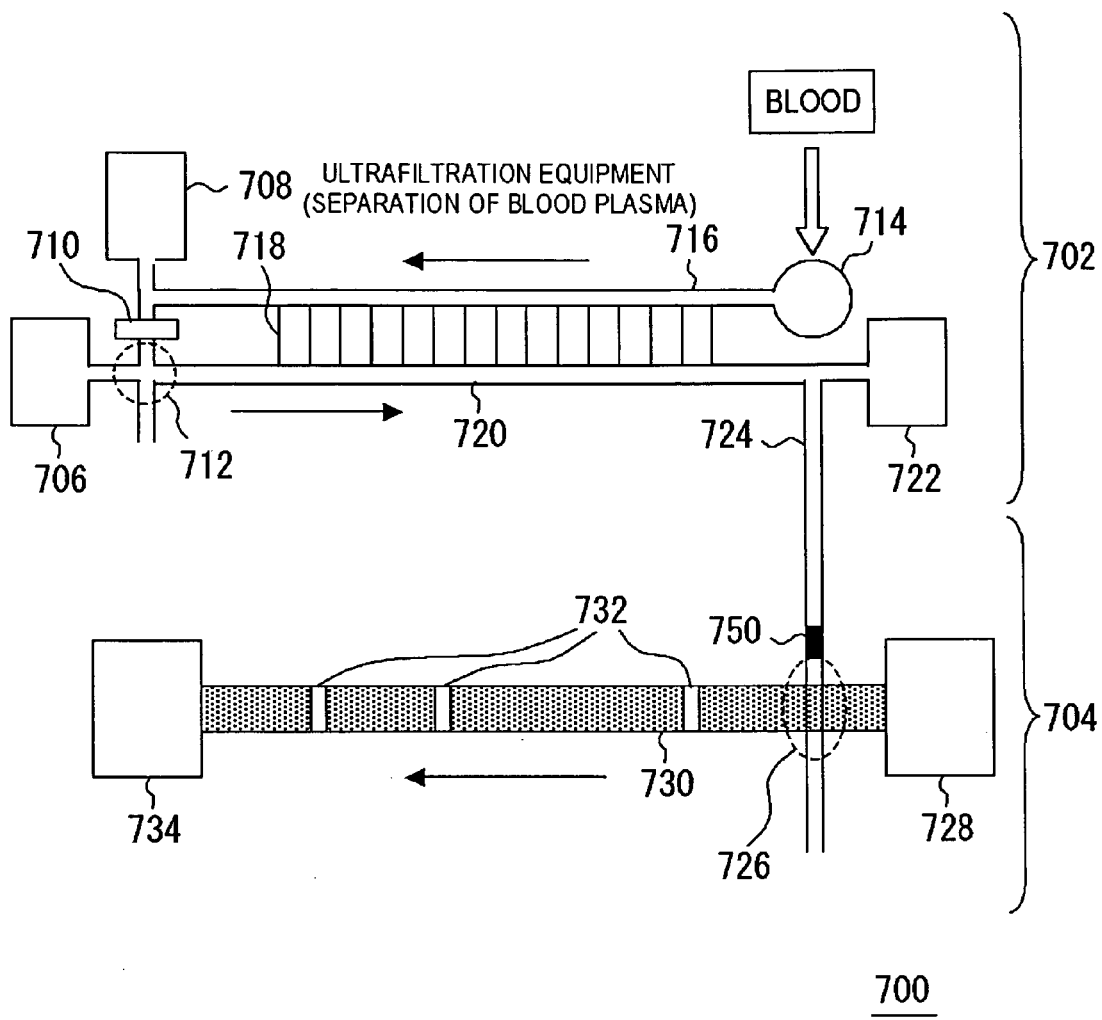
FIG. 10 is a diagram, illustrating a structure of an apparatus according to the embodiment.

FIG. 10 is schematic block-diagram of an apparatus according to the present embodiment. This apparatus is composed of an ultrafiltration system 702 and a separating apparatus 704. Ultrafiltration system 702 comprises, as main configuration elements, a first channel 716, a second channel 720 and a switch 712 disposed therebetween. The separating apparatus 704 is an apparatus that separates a sample introduced from a switch 726 by a separating portion 730 and recovers thereof from a recovering section 734. A case of conducting the separating operation by using blood as a sample will be described as follows.

Blood introduced from a sample input port 714 moves through the first channel 716 and reached to an intersection region of the switch 712 via a filter 710. This provides the "opening" status of the switch 712, and then a buffer in a buffer tank 706 enters into the second channel 720. The buffer moves toward the downstream (right side in figure) with blood plasma that has passed from the first channel 716 through a discharge portion 718, and reached to the switch 726 via the channel 724. Here, some of the sample moves to a discharge portion 722.

Switch 726 has a structure that is similar to the structure shown in FIGS. 7(*a*) to (*c*). Arrival of the buffer containing blood plasma presents the "opening" status of the switch 726. Then, as have already described in the description related to FIGS. 7(*a*) to (*c*), a specified quantity of the buffer containing blood plasma is introduced into the separating portion 730. The upstream of the switch 726 is provided with a stop valve 750, so that the configuration for preventing the flow of surplus amount of the buffer containing a blood plasma is provided.

When the buffer containing blood plasma is introduced into the separating portion 730, blood plasma is separated according to molecular weight into a plurality of bands 732 by a developing solution introduced from a buffer tank 728. Thereafter, the sample can be recovered from a recovering section 734 at an appropriate timing to obtain components fractionated by molecular weights.

The components recovered in the recovering section 734 are then pre-processed and dried, and eventually be utilized for other analysis. For example, an identification of protein by MALDI-TOFMS is conducted.

Sixth Embodiment

The present embodiment relates to a type of a switch of closing a channel when a trigger solution reaches. FIG. 11(*a*) is a schematic block diagram of a switch according to the present embodiment. A channel 901 is filled with a buffer 912, a trigger channel 902 is provided in the side surface of the channel 901, and a pump 910 is disposed in the trigger channel 902.

Pump 910 is composed of a water absorption region 908, a hydrophobic region 906 and a hydrophilic region 904. A buffer solution is stored in the hydrophilic region 904. A specific configuration of the water absorption region 908 is exemplified as follows.

(i) Configuration Being Provided with a Plurality of Columnar Member.

(ii) Configuration Being Filled with a Plurality of Porous Members or Beads.

Here, the configuration (i) is employed.

Air 915 exists in the water absorption region 908 and the trigger channel 902. The pump 910 is provided with an air opening 905, and further is connected to the channel 903, in which the trigger solution (buffer) is introduced.

When the trigger solution is introduced into the pump 910 through the channel 903 in the standby status of FIG. 11(*a*), it is leaked to the hydrophobic region 906, so that the buffer stored in the hydrophilic region 904 comes into contact with the liquid surface of the hydrophobic region 906. Then, the buffer stored in the hydrophilic region 904 moves toward the channel 901, where it is drawn in the columnar member formation region 908 by the capillary force. Then, air 915 trapped in this region is pushed to the channel 901. Air 915 functions to dam the fluidization of the buffer 912 in the channel 901, thereby providing the closing status of the switch.

Seventh Embodiment

The present embodiment relates to a reversible switch. The reversible switch means a switch that can conduct the opening and the closing operation for the channel in a reversible manner. FIG. 12(a) schematically illustrates a rough structure of a switch according to the present embodiment. In this switch, a first trigger channel 920 and a second trigger channel 926 are provided to be communicated to a side wall of a principal channel 924. A hydrophobic region 922 is provided in a position where these channels intersects. Further, a hydrophobic region 930 is provided in each of the channels as shown in the figure. These hydrophobic region has a configuration similar to that shown in FIG. 8, and is a region, in which circular hydrophobic regions are regularly formed according to a predetermined pattern. In the inside of the principal channel 924 a buffer 927 remains in the upstream (left side) rather than the hydrophobic region 922.

FIG. 12(b) illustrates a status that the trigger solution is introduced into the first trigger channel 920. In this occasion, the trigger solution contacts the buffer 927 in the hydrophobic region 922, and thus these solutions create a continuous phase. Then, the buffer 927 fluidizes toward the downstream of the right direction in the figure. In other words, the switch becomes an opening status.

Next, a bubble 928 is pushed and is introduced therein by pressurizing air in the second trigger channel 926, as in FIG. 12(c). Since the bubble 928 has a strong hydrophobicity, the switch becomes a closing status, leading to the status that the transfer of the buffer 927 stops.

When the pressurization to the second trigger channel 926 is stopped to cease the transfer of the buffer 927, the status thereof is back to the status shown in FIG. 12(a) again. Thereafter, the switch can further be turned into the opening status as shown in FIG. 12(b). In other words, the reversible operation of the switch can be achieved.

Eighth Embodiment

Figure 13:
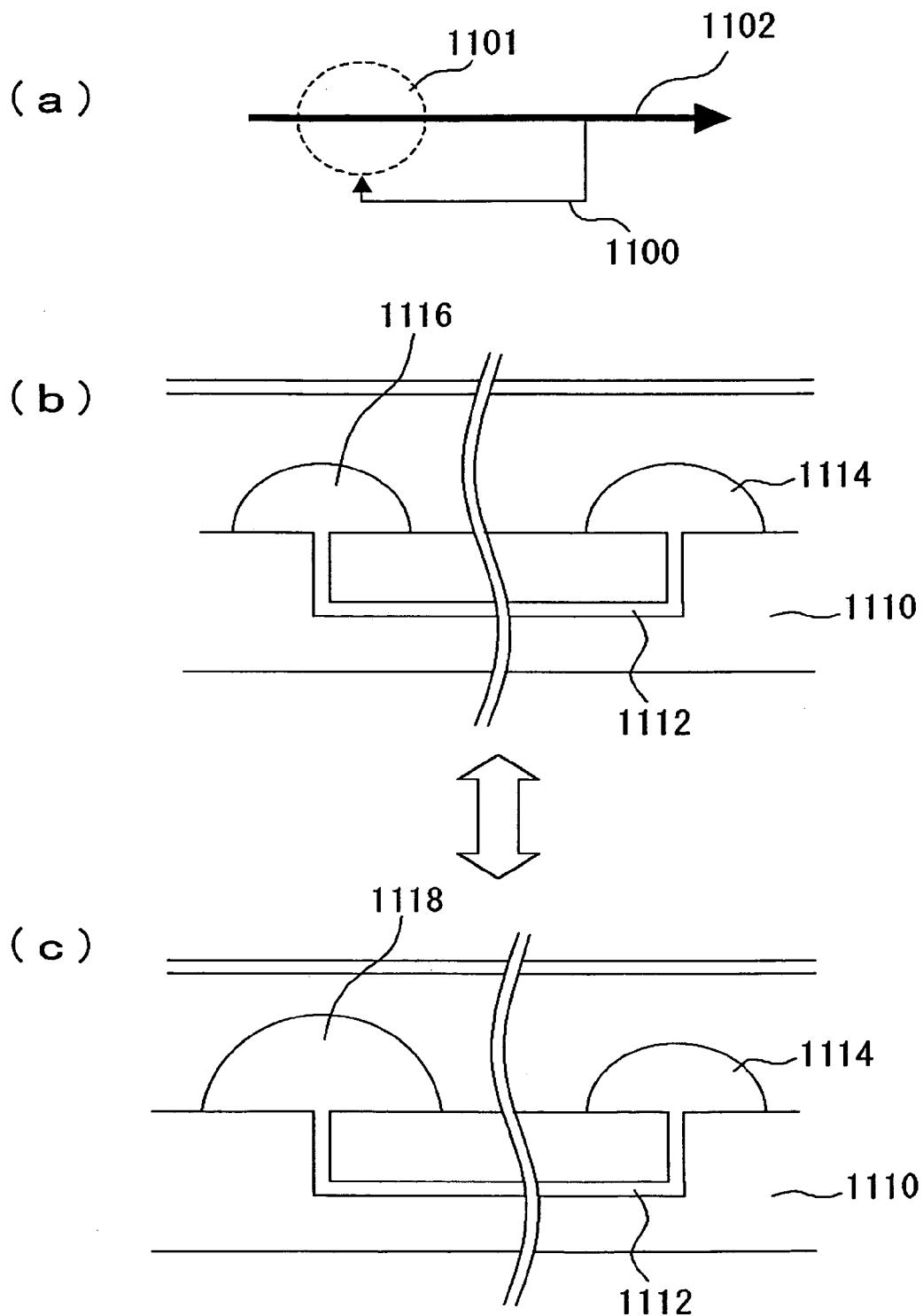
FIG. 13 is a diagram, illustrating a switch structure according to the embodiment.

The present embodiment relates to a switch having a structure, in which, as shown in FIG. 13(a), a liquid moving through a channel 1102 is transported through a secondary channel 1100 and fed to a switch 1101 located in the upstream back, thereby acting to intercept the channel 1102.

This feed-back type switch can be effectively utilized as a switch that can stop an influx of a liquid when a specified chamber is fully filled. For example, in an apparatus shown in FIG. 6, an application of preventing further inflow of a liquid when liquid reaches an intersecting point of the sample quantification tube 530 and the channel for separation 540 intersected, is possible.

FIG. 13(b) illustrates an example of a mechanism that prevent a change of flow rate by such feed-back type operation. In this mechanism, a channel 1112 is provided in a substrate 1110. The upper part of the substrate 1110 functions as a channel. The channel 1112 is filled with an inert hydrophobic liquid such as a mineral oil.

The following description will be made in reference to a case that a liquid fluidizes in the direction from left to right in the figure. The hydrophobic liquid is in a status that a small amount of the liquid is spilt from the channel 1112, and a droplet 1116 and a droplet 1114 are formed in the upstream and the downstream, respectively. When the pressure is equal in both of the upstream and the downstream, the sizes of these droplets are same, and when the channel pressure is increased in the downstream due to an increase of flow rate or the like, the size of the droplet 1114 is reduced, and as a trade off, the size of the droplet 1116 is increased to become a droplet 1118 (FIG. 13(c)). As a result, an effective cross-section of the channel is decreased, and thereby reducing the flow rate therethrough. Having such structure, an increase of the pressure in the downstream create the status of FIG. 13(b) again, and thus the normal flow condition is achieved. As described above, the fluctuation in the flow rate at respective points in the channel can be reduced.

The above-described operation is also applied to a case that a liquid fluidizes in the direction from right to left in the figure. In this case, when a reduced flow rate in the downstream provides a decreased pressure, the effective cross-section in the upstream of the channel is increased, thereby increasing the flow rate.

Ninth Embodiment

In the present embodiment, a clock line is provided in a microchip, and based on this configuration, a liquid fluidization through a channel on the chip is controlled. This embodiment will be described in reference to an example, in which a multi-sample is injected by Electrospray ionization mass spectrometry (ESI-MS). In this place, the multi-sample means a sample, which is prepared by alkylating, enzymatically digesting or desalting different types of proteins, such as, for example, a protein or a peptide contained in each spot that is preparatively isolated by two-dimensional electrophoresis.

FIGS. 14(a) and 14(b) illustrate a structure of a chip having a switch according to in the present embodiment disposed thereon. FIG. 14(a) is a plan view of this chip. A channel 1203 for flowing a first processed solution 1204 and a channel 1203 for flowing a second processed solution 1205 are formed in parallel.

A clock channel 1201 is provided along a direction being orthogonal with these channels. These include multi-layered channel structure shown in FIG. 14(b). FIG. 14(b) is a cross-sectional view of this chip.

This has a structure comprising a substrate 1220 for a principal channel and a substrate 1210 for a clock channel, both of which are laminated. A principal channel 1203 is formed on the surface of the substrate 1220 for a principal channel, and a clock channel 1201 is formed on the surface of the substrate 1210 for a clock channel. These channels are mutually connected by a channel 1212 for control. A switch 1207 is provided in the principal channel 1203.

Returning to FIG. 14(a), a fluidization of a fluid for clock introduced into the clock channel 1201 is in a status under a control by a time delay chamber 1202, and thereafter this reaches the switch 1207 via the channel 1212 for control. Then, the channel 1203 is in an opening status, such that the first processed solution 1204 is transferred toward the downstream, thereby being guided to an injector of ESI-MS.

Thereafter, the fluid for clock is transported to the downstream of the clock channel 1201, and after passing through another time delay chamber, reaches the switch 1208. Since the switch 1208 is a type of closing the channel by an arrival of a trigger, the fluid for clock functions as the trigger, leading to close the channel 1203. Thereafter, similar actions are made over the channel 1203 for flowing the second processed solution 1205, such that the second processed solution 1205 is transferred toward the downstream, thereby being guided to the injector of ESI-MS.

Concerning the fluidization of the fluid for clock in the clock channel 1201, it is precedently designed that the time required for reaching an arbitrary location in the channel can be precisely reproduced. Thus, the utilization of such clock channel allows the implementation of an arbitrary processing on the chip with improved time controllability.

Tenth Embodiment

In the present embodiment, a channel intercepted by the hydrophobic region is opened by vibrating the intercepted channel. FIG. 15(*a*) illustrates a structure of such switch. In the diagram, a damming portion 110 composed of a hydrophobic region is provided in the principal channel 101, and the liquid sample 104 is stopped at this portion. Hydrophilic substrate surface is exposed in the portions thereof except the damming portion 110. The structure of the damming portion 110 is similar to that illustrated in FIG. 8.

Under this condition, the whole microchip having the switch formed therein is vibrated. Then, the liquid sample 104 maintained in the damming portion 110 is transported beyond the damming portion 110 and to the downstream thereof, thereby presenting the opening status.

Various methods can be employed for providing vibration. FIGS. 18(*a*) and 18(*b*) indicate one example. These diagrams are cross-sectional views, observed the switch of FIG. 15(*a*) from the transverse direction. A lid 141 is provided to the channel 101, and a protrusion 140 is provided as a vibration applying unit onto the lid 141. When this protrusion 140 is broken off, vibration is given to the channel 101 so that the switch is in an opening status.

Figure 19:
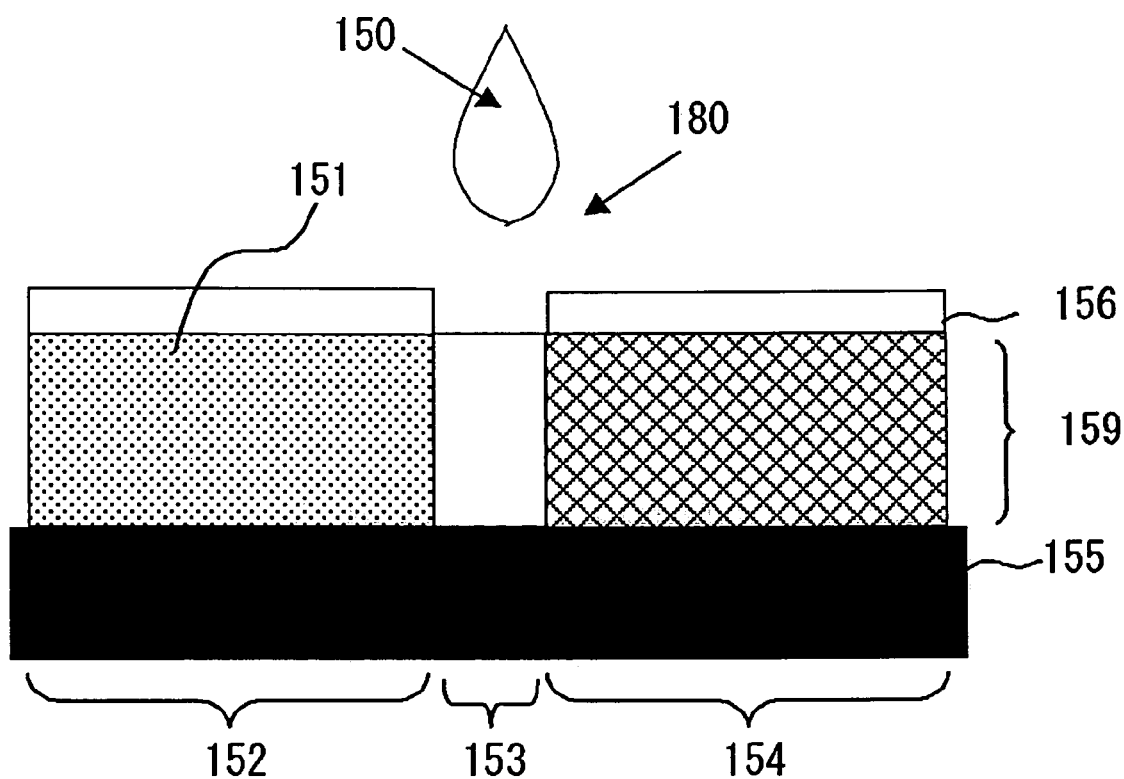
FIG. 19 is a diagram, illustrating a switch structure according to the embodiment.
Figure 20:
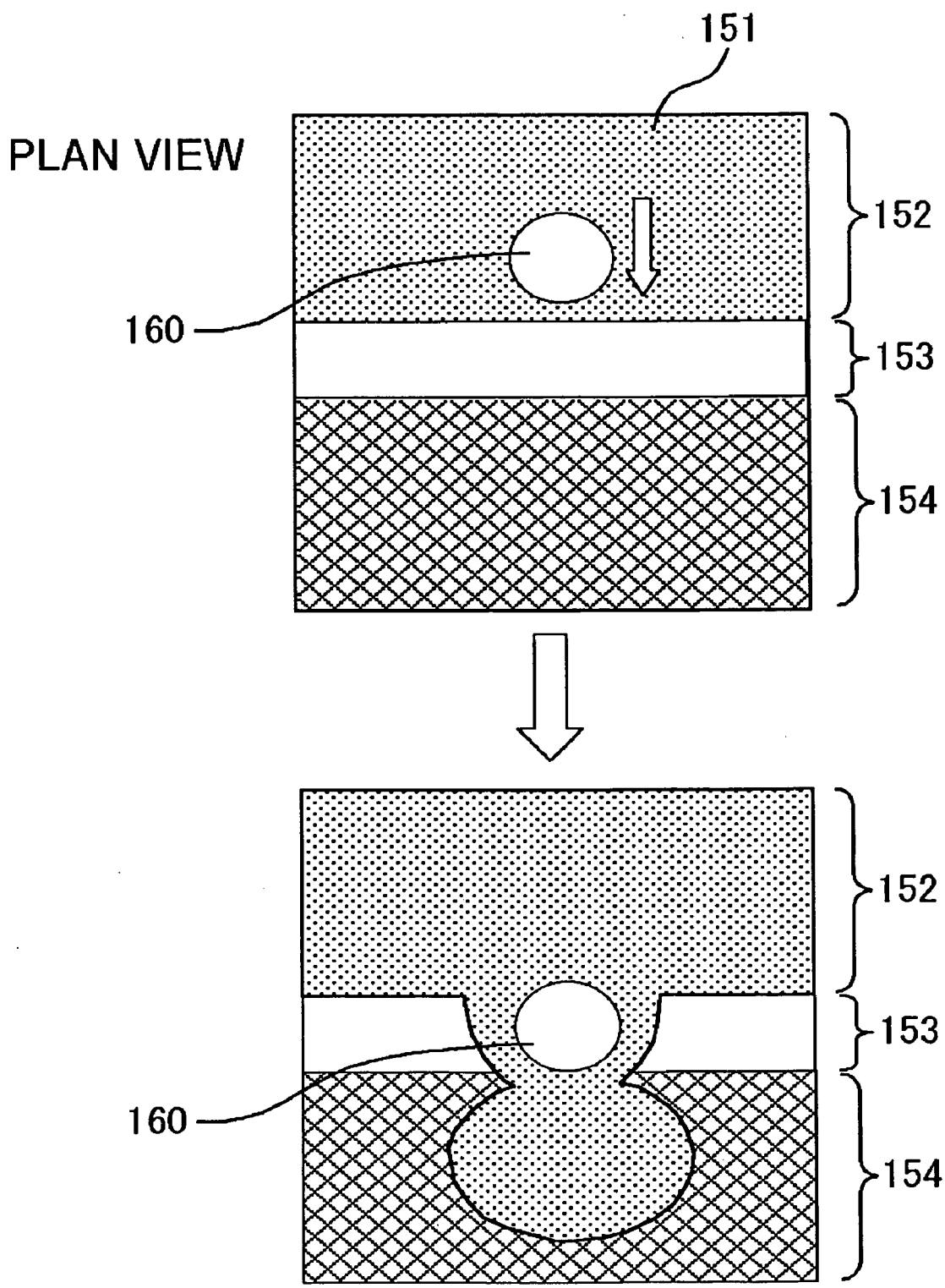
FIG. 20 is a diagram, illustrating a switch structure according to the embodiment.
Figure 23:
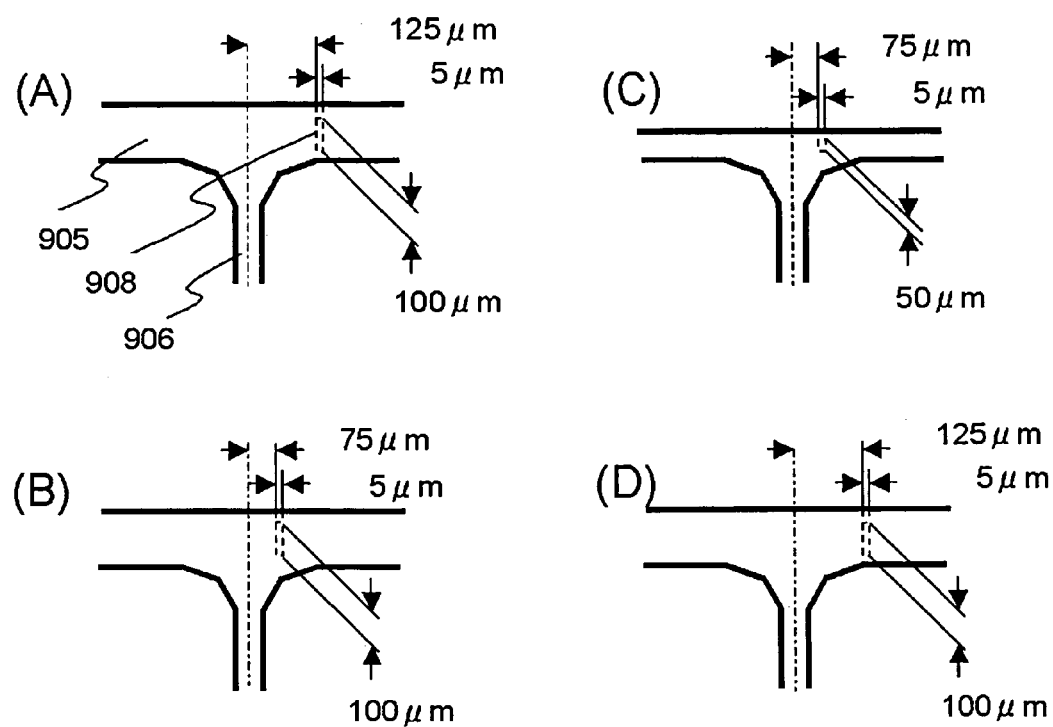
FIG. 23 is a diagram, illustrating a switch structure according to an example.

FIG. 19 and FIG. 20 indicate another example of a method for actuating the switch.

As for the FIG. 19, the switch becomes an opening status by dropping of the sample. A channel 159 is formed between the substrate 155 and the lid 156. Hydrophobic region 153 is inserted between a water retention region 152 and a water absorption region 154. An aqueous solution is stored in the water-retention region 152 under suitably pressurized condition. It is dammed by the hydrophobic region 153. The water-retention region 152 is joined to the water absorption region 154 by dropping the hydrophilic sample 150 such as blood on the hydrophobic region 153, thereby commencing a fluidization thereof from left to right in the diagram.

FIG. 20 shows an example employing a moving member. Hydrophobic region 153 is inserted between a water retention region 152 and a water absorption region 154.

The water-retention region 152 stores an aqueous solution, and is dammed by the hydrophobic region 153. A magnetic material 160 having a surface hydrophilicity is initially located in the water-retention region 152, and then is transported to a location lying across the water-retention region 152 and the water absorption region 154 by externally operating thereof by a magnet, the water-retention region 152 is joined to the water absorption region 154 via the hydrophilic surface of the magnetic material 160, thereby commencing the fluidization from the top to the bottom in the diagrams. In the present embodiment, the diameter of the magnetic material 160 is selected to be not smaller than the width of the hydrophobic region 153. Having such configuration, switch can be well operated.

Eleventh Embodiment

Figure 16:
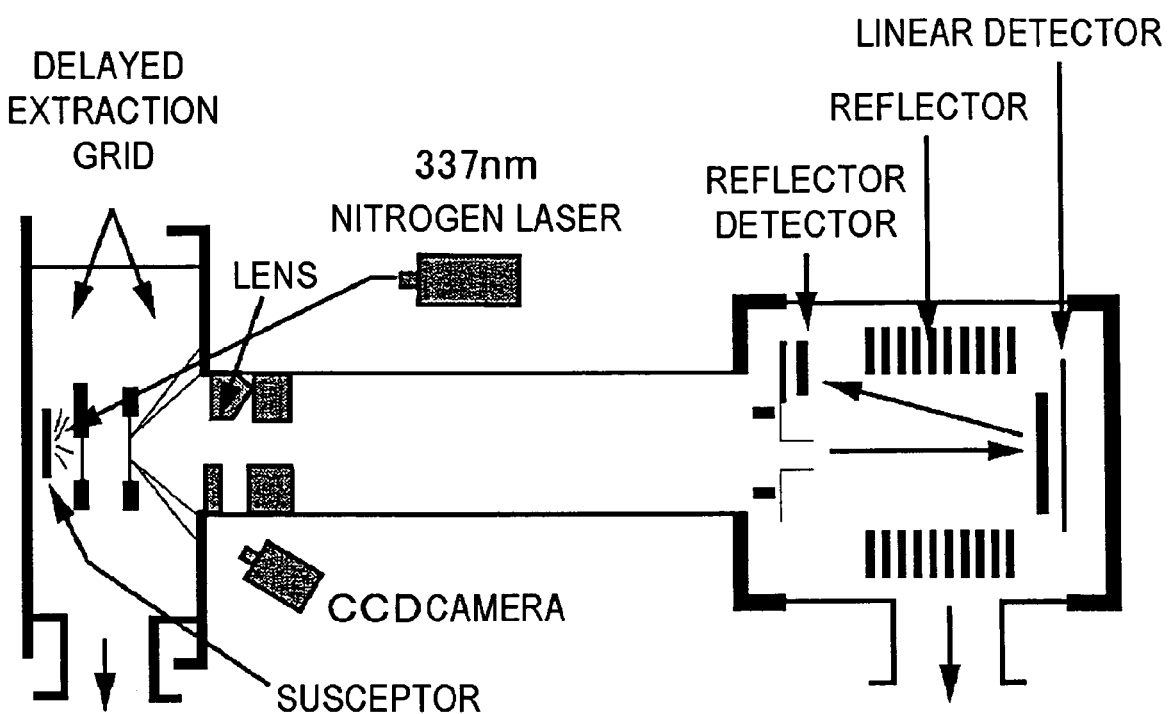
FIG. 16 is a schematic diagram, illustrating a configuration of a mass spectrometry apparatus.

FIG. 16 is a schematic diagram illustrating a configuration of a mass spectrometry apparatus. In FIG. 16, a dried sample is mounted on a susceptor. Then, the dried sample is irradiated with a nitrogen gas laser beam having a wave length of 337 nm under a vacuum condition. Then, the dried sample vaporizes together with the matrix. The susceptor also functions as an electrode, and thus the vaporized sample flies in the vacuum by applying an electrical voltage, and is detected by a detecting unit comprising a reflector detection device, a reflector and a linear detection device.

Figure 17:
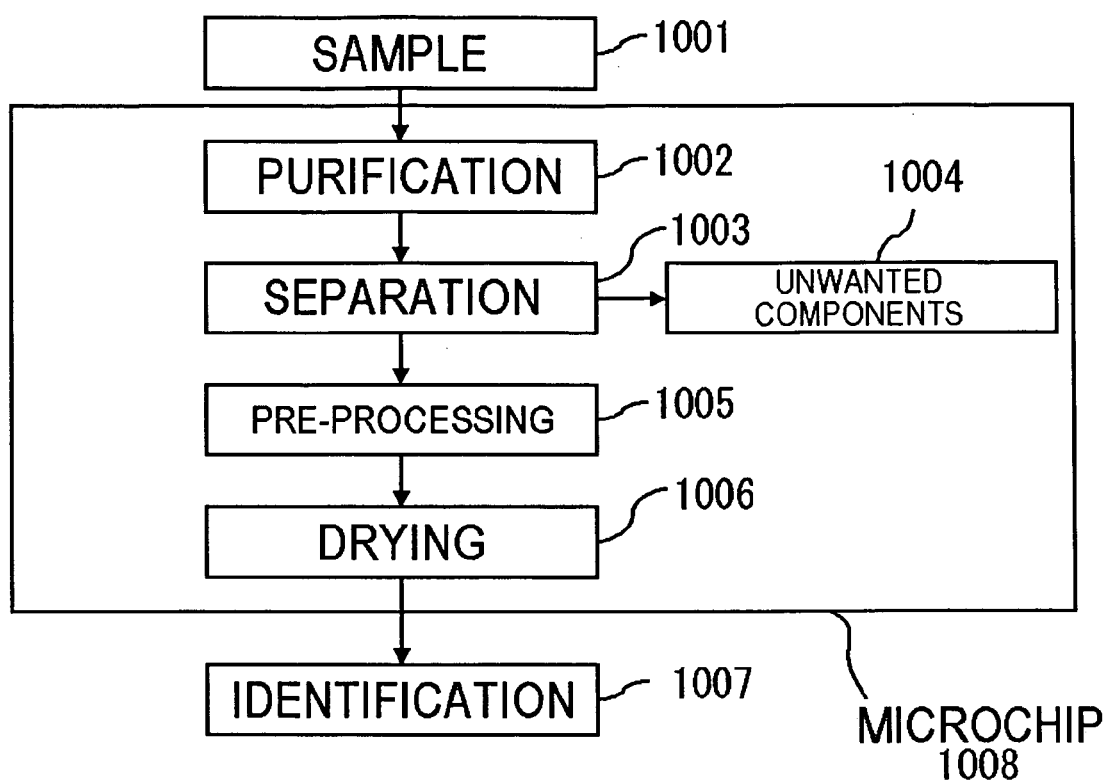
FIG. 17 is a block diagram of the mass spectrometry system.

FIG. 17 is a block diagram of a mass spectrometry system including a dryer of the present embodiment. This system comprises units for conducting respective processes of a purification 1002 for removing foreign elements in a sample 1001 in a certain level, a separation 1003 for removing unwanted components 1004, a pre-processing 1005 of the separated sample, and a drying 1006 of the sample after the pre-processing.

A portion or whole of these units can be mounted onto one, two or more microchips 1008. The identification of trace amount of a component can be definitely conducted with higher efficiency via the method with less loss by sequentially conducting the processes of the sample on one microchip 1008.

In the above-described embodiment, the damming portion may preferably be positioned at a location in vicinity of the trigger channel. More specifically, by assuming that a point where the center line of the principal channel intersects with the center line of the trigger channel is defined as an intersecting point, it is preferable to take a distance between the intersecting point and the hydrophobic processed portion as equal to or less than 1.5 times of the width of the trigger channel, and more preferably equal to or less than the width of the trigger channel. Having such configuration, stable switch operation I can be achieved.

EXAMPLES

Example 1

In the present example, a confirmation of the "on" operation of the liquid switch was conducted.

In the present example, it was further confirmed that the liquid switch can be presented by a patterned channels formed by drawing the pattern with a hydrophobic ink, without digging thereof into a groove for the channel.

A structure of a chip is shown in FIGS. 21(*a*) and 21(*b*). FIG. 21(*a*) is a photography showing a planar structure thereof, and 21(*b*) shows a cross-sectional view thereof. A hydrophilic slide glass 800 (ground-edge white frosted slide glass or "Hakuenma furosuto suraido garasu", pre-cleaned, commercially available from Matsunami Glass Ind., Ltd., contact angle with water is about 7 degrees) was employed as a substrate, and an oil-based pen for glass (commercially available from Zebra Co., Ltd., No. YYF1, under the trade name of "CHO GANKO SHIKKARI MARKER", contact angle with water is about 70 degrees or, commercially available from Pentel Co., Ltd., No.X100W-SD, under the trade name of "Pentel White", contact angle with water is about 100 degree) was employed to draw thereon a portion of a principal channel 805 having a width of 5 mm, a portion of a trigger channel 806 having a width of 1 mm and patterned channels 809 including a hydrophobic processed portion 808.

The channel portion was achieved by tracing a circumference thereof with the pen point having a width of 1 mm to 2 mm. Since water was repelled by the hydrophobic region, water flowed only through a space between the lines of the patterned channel 809. hydrophobic processed portion 808 for stopping the liquid in the principal channel 805 was presented by drawing the line having a width of about 80 μm with a pen, a tip of which had been sharpened.

Then, a double sided tape 801 having a thickness of about 0.3 mm (commercially available from Nitoms Co., Ltd.) was adhered as a spacer, and a cover glass 804 having a hydrophobic surface (Matsunami micro cover glass thickness 0.17-0.25 mm, silicone coated 20×20 mm, as a spacer, commercially available from Matsunami Glass Ind., Ltd., contact angle with water is about 85 degrees) was installed thereon. A longitudinal gap 803 created by the above operation having a depth of about 0.3 mm and a transverse gap sandwiched by the patterned hydrophobic channel 809 together formed the principal channel 805 and the trigger channel 806.

This chip was employed by being installed on a horizontal table. FIGS. 22(*a*), 22(*b*), 22(*c*) and 22(*d*) are serial photography showing the switch operation of this chip. FIG. 22(*a*) shows an initial state. FIG. 22(B) is a photograph showing a status after introducing a black ink 807 diluted in 10 times (SPS-400# 1, commercially available from Platinum Pen Co., Ltd.) from a right edge of the principal channel. The black ink 807 automatically entered into the principal channel 805 by a capillary effect, and thereafter stopped at the hydrophobic processed portion 808, where the conditions thereof was maintained. Two minutes later, water 810 (tap water) was introduced into an end of the trigger channel 806. FIG. 22(*c*) is a photograph showing the status just after that operation. The water 810 rapidly entered into the trigger channel 806 by a capillary effect, and in the next moment, the liquid level thereof was fused with the liquid level of the black ink 807 stopped at the hydrophobic processed portion 808. This provided the liquid level proceeding beyond the hydrophobic processed portion 808, and thus the black ink 807 was transported through the principal channel 805 toward the left side. (FIG. 22(*d*)) Meanwhile, a phenomenon of a backflow of the black ink 807 in the principal channel 805 toward the direction to the trigger channel 806, or a phenomenon of further flow out of the water 810 in the trigger channel 806 toward the direction to the principal channel 805 were not observed.

It is considered that this is because the width of the trigger channel 806 is narrower as compared with the width of the principal channel 805, leading the channel resistance thereof to be larger.

From the above-described results, it was shown that even the principal channel 805 having the macro sized width of 5 mm was employed, the principal channel could be opened with the trigger channel 806 having narrower width than the principal channel, and further that the channel constituting the switch could be presented only by drawing the edge with hydrophobic ink on the hydrophilic surface without digging thereof into a groove.

Example 2

In the present example, a confirmation of the "on" operation of the liquid switch with the narrower channels on the order of from 10 μm to 100 μm was conducted. Further, the liquid switch of the present example was manufactured for a trial by a photolithography, which means that a channel system including a number of liquid switch can be integrated on the chip of several cm-square.

FIGS. 23(A) to (D) are plan views illustrating a structure of a liquid switch produced for a trial. An object looks like a T-shape is a groove dug on the silicon substrate 900 by a method discussed later.

It was provided with a transversely extending principal channel 905, a trigger channel 906 normally intersecting thereof and a hydrophobic processed portion 908 located on the right side of the principal channel 905 over the intersecting point. Four types of the switches were provided corresponding to the thickness of the channel, the width and the installation position of the hydrophobic processed portion 908 and the direction for introducing the liquid into the principal channel. Respective types are referred to the alphabetic character (A) to (D) of FIG. 23.

Type (A) was provided with a principal channel of 100 μm and a trigger channel of 50 μm, and as a control, the liquid was introduced from the left side, which is an inverse direction of the hydrophobic portion 908. (in types (B), (C) and (D), the liquid was introduced from the right side, where the hydrophobic processed portion 908 is also located.) p Type (B) was provided with a principal channel of 100 μm and a trigger channel of 50 μm, and further provided with a hydrophobic portion 908 having a width of 5 μm and partially including chipped-off portions just before an intersecting portion. Although the hydrophobic portion 908 is not visible due to its transparency, it is indicated in the plan view of FIG. 23 with a dotted line.

Type (C) was provided with a principal channel of 50 μm and a trigger channel of 100 μm, and further provided with a hydrophobic portion 908 having a width of 5 μm and partially including chipped-off portions just before an intersecting portion, and Type (D) was provided with a principal channel of 100 μm and a trigger channel of 50 μm, and further provided with a hydrophobic portion 908 having a width of 5 μm in a position being remote from an intersecting portion.

Although it is not shown in the diagrams, liquid receivers of 1 mm-square was formed at the edge of respective channels by the etching process that simultaneously formed the channels.

These liquid switches were experimentally manufactured by the following process.

[Trial Manufacture of Liquid Switch]

(1) Photolithography and Wet Etching of Channel Portion

Thermal oxidation was conducted on the entire surface of a clean (110) silicon substrate to form a thermal oxidation film of 2000 A(angstrom). Next, a photo resist (S1818, commercially available from Shipley Far East Inc.) is applied, and then an exposing and a developing were carried out by employing quartz chrome masks, on which channel patterns of the liquid switches for the aforementioned types (A) to (D) were depicted, and finally the photo resist of the channel pattern was removed to expose the oxide film. Then, the exposed oxide film was removed with a buffered fluorinated acid (16 buffered fluorinated acid, commercially available from Morita Kagaku Kogyo Co., Ltd.) to expose the silicon surface. Subsequently, the photo resist remained on the substrate was completely stripped by cleaning with acetone and ethanol, and after the water rinsing and drying, an etching was carried out for about 20 minutes with 25% Tetramethyl ammonium hydroxide (TMAH) heated up to 90 degree C. to obtain the silicon substrate having the patterned channels etched to about 20 μm depth.

This was dipped in the buffered fluorinated acid to remove the remained thermal oxidation film.

While the principal channel 905 or the like has a width of 100 μm on the mask, the width is increased by 10% to 20% after the etching. Similar discussion can also be made for the trigger channel.

(2) Chemical Oxidation of Silicon Substrate

Since the surface of the silicon substrate having such patterned channels etched thereon was hydrophobic, it was dipped in a concentrated nitric acid solution at a temperature of 90 degree C. for 40 minutes in order to provide a hydrophilicity thereto. The substrate surface after the rinsing was hydrophilic, and thus it was confirmed that water satisfied the channel with the capillary effect.

(3) Installation of Hydrophobic Processed Portion 908

A thin film photo resist (S1805, commercially available from Shipley Far East Inc.) was dropped directly on the silicon substrate having the surface that had acquired the hydrophilicity by the above-described chemical oxidation to carry out a spincoating. Then, a quartz chrome mask having an opening in the portion of the hydrophobic processed portion 908 was employed, and the exposing and the developing were conducted after an alignment. This exposed only the hydrophobic processed portion 908 on the channel surface. This substrate was disposed within a stainless steel container, and after dropping silazane so as not to contract the substrate, the container was tightly sealed, and is left for a night and day. Vaporized silazane formed a hydrophobic silazane film on the hydrophobic processed portion 908. (This film is resistance over acetone and ethanol cleaning)

Just before the experiment, the thin film photo resist adhered on the substrate was removed with acetone and ethanol, and after rinsing with water for not shorter than ten minutes, drying was conducted with an air gun. Lid was not provided onto the upper surface of the channel, and was used in an opening status.

EXPERIMENTS

The substrate experimentally prepared by the method described above was horizontally mounted on a stage of a metaloscope, and serial picking-up was carried out via video (Sony Digital Handycam, commercially available from Sony) by employing an object lens of 5 magnifications or 10 magnifications and a video system through charge coupled device (CCD) attached to the body tube.

As the liquids for flowing into the channel, two types of liquid were prepared, i.e., a colorless solution containing a surfactant (NCW-610A, commercially available from Wako Pure Chemical Industries Co., Ltd.) diluted to 1000 folds with distilled water and a pigment solution containing a black ink (SPS-400 # 1, commercially available from Platinum Pen Co., Ltd.) diluted to 10 folds using the colorless solution. The reason for employing thin surfactant is to avoid a problem, in which the inflow rate to the channel is extremely low when distilled water is employed, and the channel is dried on the way due to the absence of the lid. It may be considered that the reason for lower inflow rate is probably that the application of the thin film photo resist deteriorates the hydrophilicity of the substrate surface to some extent. Sufficient inflow rate (about 500 μm/sec) could be achieved by employing thin surfactant.

Figure 24:
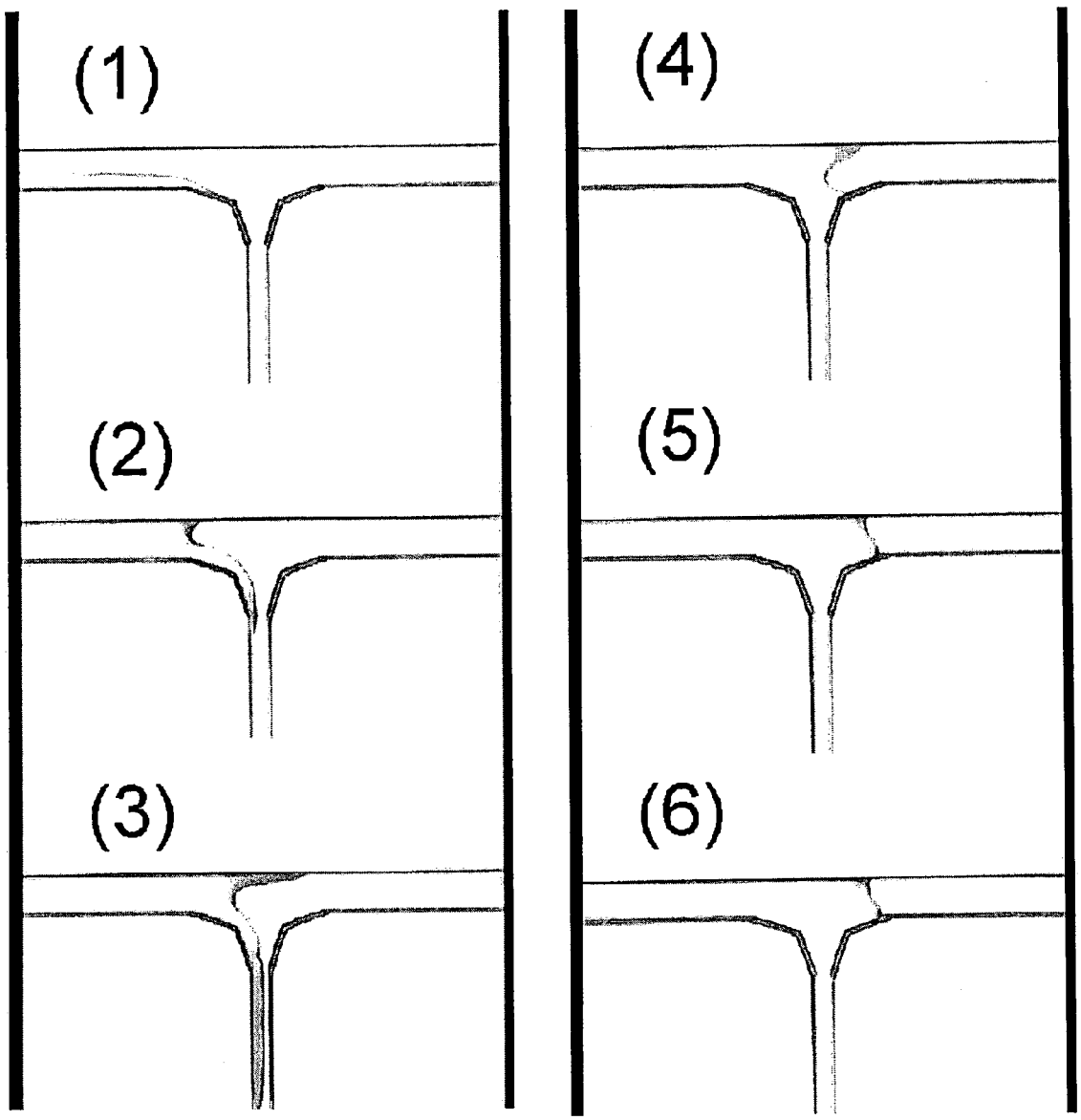
FIG. 24 is a diagram for describing an operation of the switch according to an example.

FIGS. 24(1) to 24(6) includes serial photography showing conditions after the colorless solution was introduced into the liquid switch of type (A) from the left side that is an opposite side to the side of the hydrophobic processed portion 908 (object lens: 10 magnifications). As shown in FIGS. 24(1) to 24(6), the colorless solution automatically entered into the principal channel 905, and after proceeding beyond the intersecting point, stopped at the hydrophobic processed portion 908. It can be seen from these results that the hydrophobic processed portion 908 has an advantageous effect for stopping the solution FIGS. 25(1) to 25(6) include serial photography showing conditions after the pigment solution was introduced into the principal channel 905 of the liquid switch of type (B) from the right side (object lens: 10 magnifications).

Figure 25:
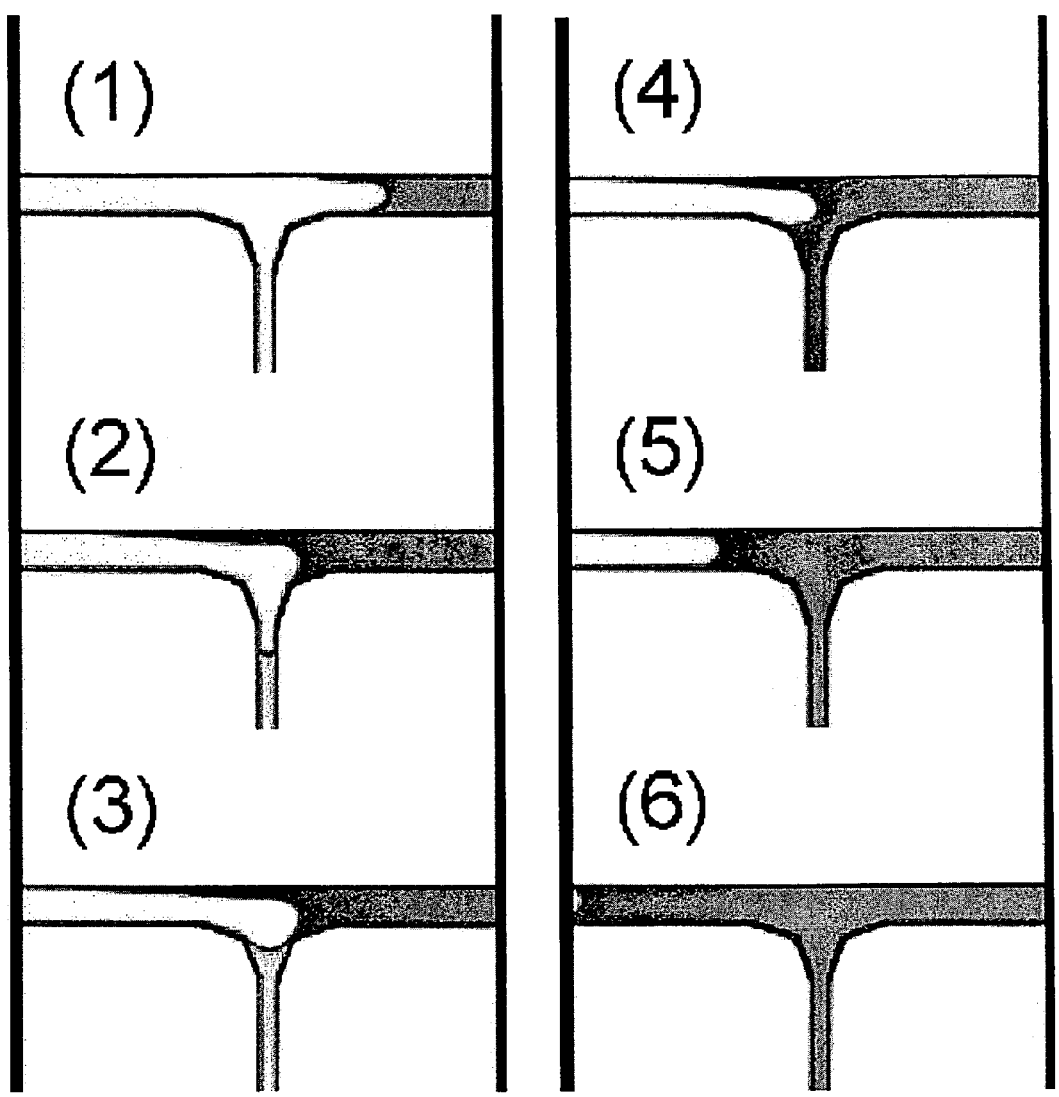
FIG. 25 is a diagram for describing an operation of the switch according to an example.

The pigment solution automatically entered into the principal channel 905 (FIG. 25(1)), and thereafter the main flow stopped at the hydrophobic processed portion 908. A portion of the pigment solution escaped through gap between the hydrophobic processed portion 908 and the channel wall to reach a point beyond the intersecting point, but no longer moved further (FIG. 25 (2)).

Next, when the colorless liquid was introduced into the trigger channel 906, the colorless liquid automatically entered therein, and reached to the intersecting point, and thereafter the liquid level thereof fused with the liquid level of the pigment solution that had stopped in advance (FIG. 25(3)). Thereafter, the pigment liquid proceeded beyond the hydrophobic processed portion 908, and continued to proceed through the principal channel 905 located in the left side than the intersecting point.

It can be seen from the results that the stopping effect of the hydrophobic processed portion 908 is lost by the liquid feeding from the trigger channel 906, even in the case of using the channel of not thicker than 1 mm, thereby opening the principal channel 905, or in other words "on" operation can be achieved.

Figure 26:
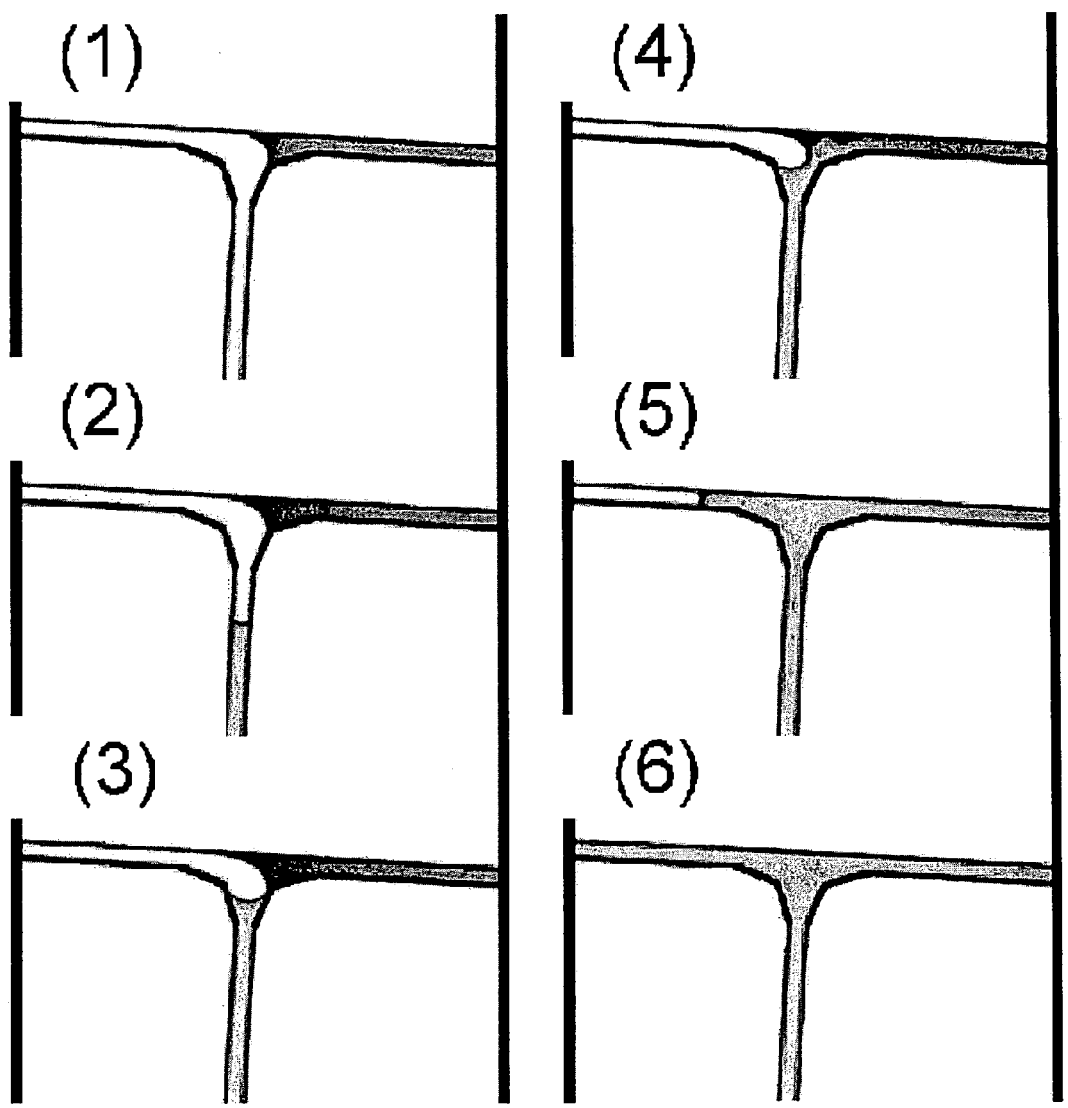
FIG. 26 is a diagram for describing an operation of the switch according to an example.

FIGS. 26(1) to 26(6) include serial photography showing conditions after the pigment solution was introduced into the principal channel 905 of the liquid switch of type (C) from the right side (object lens: 5 magnifications). Similarly as in the case of type (B), the pigment solution stopped at the hydrophobic processed portion 908 (FIG. 26(1)). When the colorless liquid was supplied from the trigger channel 906, the colorless liquid was fused with the liquid level of the solution that had stopped at the intersecting point (FIG. 26(4)), the fused liquid level began the transportation again, and proceeded beyond the intersecting point of the principal channel 905 toward the left side of the principal channel 905. However in this case, what moved through the principal channel 905 was not the pigment solution, but was the colorless liquid that was supplied from the trigger channel 906. It can be seen from the results that the switch operation may not be achieved, depending on the relationship of the thickness of the principal channel 905 and the thickness of the trigger channel 906, or depending on the quantity of supplied liquid.

Figure 27:
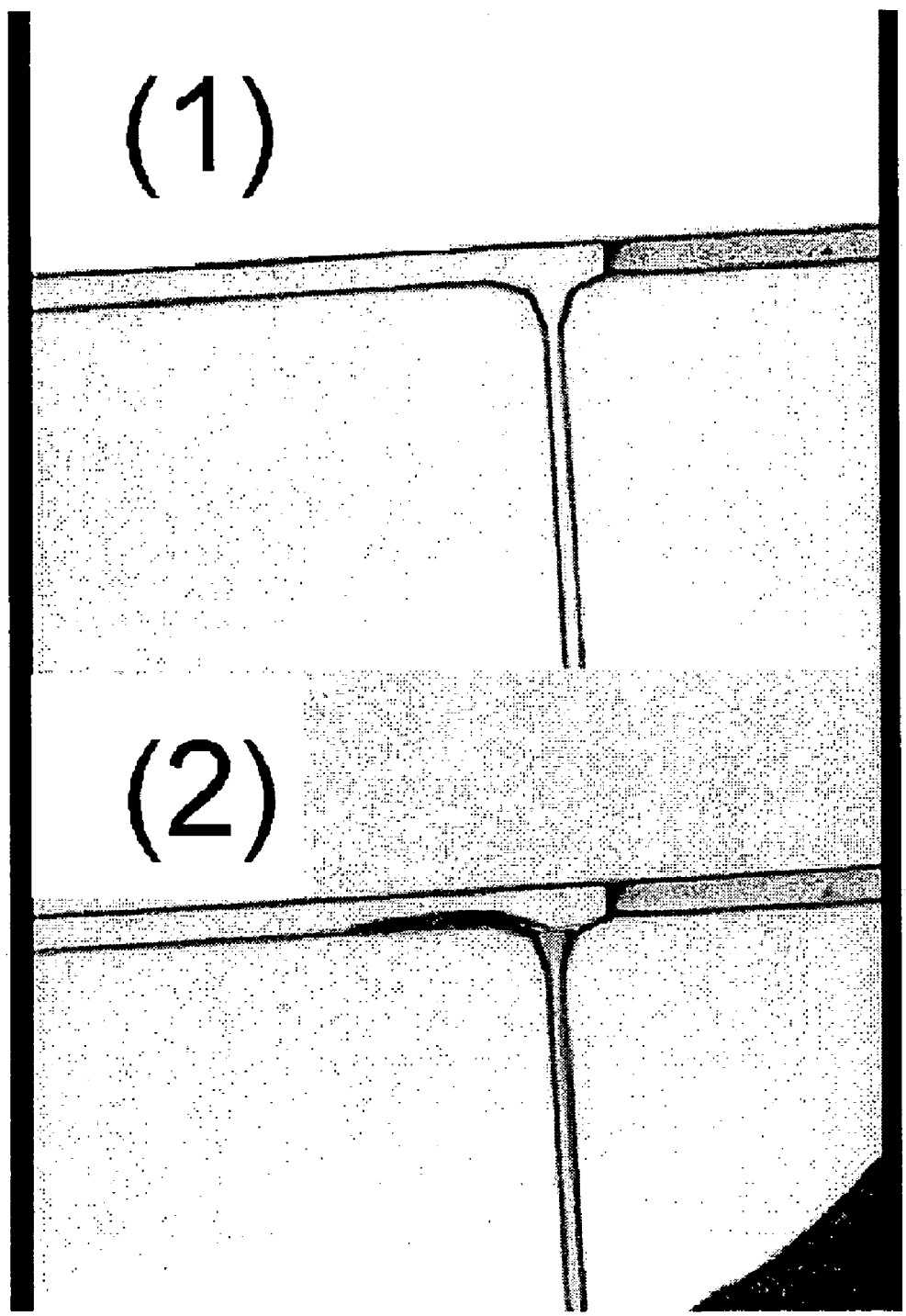
FIG. 27 is a diagram for describing an operation of the switch according to an example.

FIGS. 27(1) and 27(2) include serial photography showing conditions after the pigment solution was introduced into the principal channel 905 of the liquid switch of type (D) from the right side (object lens: 5 magnifications). The pigment solution automatically entered into the principal channel 905, and thereafter stopped at the hydrophobic processed portion 908 (FIG. 27(1)). Next, when the colorless liquid was introduced into the trigger channel 906, the colorless liquid was not sufficiently guided to the hydrophobic processed portion 908, and thus the switch operation was somewhat instable (FIG. 27(2)).

It can be seen from the results that it is preferable to dispose the hydrophobic processed portion 908 at a location in vicinity of the intersecting point. By assuming that a point where the center line of the principal channel 905 intersects with the center line of the trigger channel 906 is defined as an intersecting point, it is preferable to take a distance between the intersecting point and the hydrophobic processed portion 908 as equal to or less than 1.5 times of the width of the trigger channel 906, and more preferably equal to or less than the width of the trigger channel 906. Having such configuration, stable switch operation can be achieved. In the above-described examples, the above-described distance was 50 µm, and the width of the trigger channel 906 was on the order of 50 to 60 µm for (B) and (C). For (D), the above-described distance was 100 µm, and the width of the trigger channel 906 was on the order of 50 to 60 µm.

Summarizing the above descriptions, preferable advantages are: "on" operation of the liquid switch can be achieved even in the case of using the channel of not thicker than 1 mm; and integration can be achieved, as it can be produced via the photolithography technique, and it is preferable to consider the position of the intersecting point with the hydrophobic processed portion 908 and the surface activity of the solution, in order to achieve the stable "on" operation.

What is claimed is:

1. A liquid switch, comprising:
    a channel for flowing a first liquid therethrough; a damming portion provided in said channel for damming said first liquid; and
    a trigger channel communicated into said channel at a position of said damming portion or of downstream thereof for guiding a second liquid to said damming portion.

2. The liquid switch according to claim 1, wherein said damming portion includes a member for holding said first liquid.

3. The liquid switch according to claim 2, wherein a channel surface area per channel unit volume in said damming portion is larger than a channel surface area per channel unit volume in other portions of the channel.

4. The liquid switch according to claim 2, wherein said member holding said first liquid is a plurality of particles.

5. The liquid switch according to claim 2, wherein said member holding said first liquid is a porous member.

6. The liquid switch according to claim 2, wherein said member holding said first liquid includes a plurality of protruding portions that are separately arranged.

7. The liquid switch according to claim 2, wherein said damming portion includes a region exhibiting a lyophobicity for said first liquid.

8. The liquid switch according to claim 7, further comprising a region exhibiting a lyophobicity for said first liquid at a downstream of an intersecting point in said channel where said channel intersects with and said trigger channel.

9. The liquid switch according to claim 1, wherein said liquid switch is configured to include a valve structure in said trigger channel, and wherein said valve structure is actuated once a specified quantity of the second liquid is introduced, to closedown said trigger channel.

10. A microchip, comprising:
    a substrate;
    a sample channel formed on said substrate for passing a sample therethrough; and
    sample separating portion provided in said sample channel,
wherein the liquid switch according to claim 1 is disposed in said sample channel, and a feeding of said sample from said sample channel to said sample separating portion is controlled with said liquid switch.

11. A mass spectrometry system, comprising:
    a separating unit that separates biological sample according to molecular size or a property thereof;
    a pre-processing unit that conducts a pre-processing including an enzymatic digestion processing for the sample separated by said separating unit;
    a drying unit that dries the preprocessed sample; and
    a mass spectrometry unit that conducts mass spectrometry of the dried sample,
wherein said separating unit includes the microchip according to claim 10.

12. A microchip, comprising:
    a substrate;
    a liquid channel formed on said substrate for flowing a liquid therethrough; and
    a reaction portion provided in said liquid channels, wherein the liquid switch according to claim 1 is disposed in said liquid channel, and a feeding of said liquid from said liquid channel to said reaction portion is controlled with said liquid switch.

13. A mass spectrometry system, comprising:
    a separating unit that separates biological sample according to molecular size or a property thereof;
    a pre-processing unit that conducts a pre-processing including an enzymatic digestion processing for the sample separated by said separating unit;
    a drying unit that dries the preprocessed sample; and
    a mass spectrometry unit that conducts mass spectrometry of the dried sample,
wherein said pre-processing unit includes the microchip according to claim 12.

14. The microchip according to claim 12, further comprising: a reservoir communicating with said reaction portion, for being introduced with an agent,
    wherein said liquid switch is disposed in a liquid channel extending from said reservoir to said reaction portion, and an introduction of said agent from said reservoir into said reaction portion is controlled with said liquid switch.

15. The microchip according to claim 14, wherein said agent is an enzymatic digestion solution.

16. The microchip according to claim 15, wherein said enzymatic digestion solution is a tryptic digestion solution.

17. A microchip, comprising:
    a substrate;
    a principal channel formed on said substrate for flowing a liquid therethrough;
    a clock channel for controlling a timing of said liquid passing a predetermined point in said principal channel; and
    a control channel communicating with said principal channel and said clock channel,
wherein the liquid switch according to claim 1 is disposed in said control channel, and a transfer of said liquid in said principal channel is controlled with said liquid switch.

18. A mass spectrometry system, comprising:
    a separating unit that separates biological sample according to molecular size or a property thereof;
    a pre-processing unit that conducts a pre-processing including an enzymatic digestion processing for the sample separated by said separating unit;
    a drying unit that dries the preprocessed sample; and
    a mass spectrometry unit that conducts mass spectrometry of the dried sample,
wherein said separating unit, said pre-processing unit or said drying unit includes the microchip according to claim 17.

19. A liquid switch, comprising:
a channel for flowing a liquid therethrough; and
a damming portion provided in said channel for damming said liquid;
wherein said damming portion includes a member holding said liquid.

20. The liquid switch according to claim 19, wherein a channel surface area per channel unit volume in said damming portion is larger than a channel surface area per channel unit volume in other portions of the channel.

21. The liquid switch according to claim 19, wherein said member holding said liquid is a plurality of particles.

22. The liquid switch according to claim 19, wherein said member holding said liquid is a porous member.

23. The liquid switch according to claim 19, wherein said member holding said liquid includes a plurality of protruding portions that are separately arranged.

24. A liquid switch, comprising:
a channel for flowing a liquid therethrough; and
a damming portion provided in said channel for damming said liquid;
wherein said damming portion includes a surface exhibiting a lyophobicity for said liquid.

25. The liquid switch according to claim 24, further comprising a moving member movably disposed between said damming portion and a place except said damming portion in said channel,
wherein said moving member has a surface exhibiting a lyophilicity for said liquid, and that a position of said moving member can be adjusted from outside of said channel.

26. The liquid switch according to claim 25, further comprising a positioning unit that adjusts the position of said moving member from outside thereof,
wherein one of said moving member and said positioning units, is a magnet and the other is a magnetic material.

27. A liquid switch, comprising:
a channel for flowing a first liquid therethrough;
a secondary channel communicating with said channel;
a chamber communicating with said secondary channel; and
a trigger channel communicating with said chamber and for introducing a second liquid into said chamber,
wherein a lyophobic material exhibiting a lyophobicity for said first liquid is stored in an interior of said chamber, and
wherein said liquid switch is configured that said lyophobic material is introduced from said chamber into said channel once the second liquid is introduced from said trigger channel into said chamber.

28. The liquid switch according to claim 27, wherein said chamber comprises:
a first compartment communicating with said secondary channel;
a second compartment for storing said lyophobic material; and
a separating portion disposed between said first compartment and said second compartment for separating the compartments,
wherein said trigger channel communicates with said separating portion, and said liquid switch is configured that said lyophobic material moves from said first compartment to said second compartment once the second liquid is introduced from said trigger channel.

* * * * *